US012753396B2

(12) United States Patent
Liebig et al.

(10) Patent No.: US 12,753,396 B2
(45) **Date of Patent: *Oct. 6, 2026**

(54) CARBOXYLIC ACID ESTERS OF XYLITOL AND PROCESS FOR ENZYMATICALLY PREPARING SAME

(71) Applicant: Evonik Operations GmbH, Essen (DE)

(72) Inventors: Stefan Julian Liebig, Duesseldorf (DE); Jan Marian von Hof, Bochum (DE); Thomas Böhmer, Muelheim an der Ruhr (DE); Thomas Thomalla, Essen (DE); Kathrin Daniela Brandt, Duesseldorf (DE); Christian Hartung, Essen (DE); Hans Henning Wenk, Muelheim an der Ruhr (DE); Maxim Yavorsky, Witten (DE); Sunay Karacocuk, Herne (DE)

(73) Assignee: Evonik Operations GmbH, Essen (DE)

( * ) Notice: Subject to any disclaimer, the term of this patent is extended or adjusted under 35 U.S.C. 154(b) by 681 days.

This patent is subject to a terminal disclaimer.

(21) Appl. No.: 17/757,711

(22) PCT Filed: Dec. 17, 2020

(86) PCT No.: PCT/EP2020/086737

§ 371 (c)(1),
(2) Date: Jun. 17, 2022

(87) PCT Pub. No.: WO2021/122972

PCT Pub. Date: Jun. 24, 2021

(65) Prior Publication Data

US 2023/0033620 A1 Feb. 2, 2023

(30) Foreign Application Priority Data

Dec. 20, 2019 (EP) .................................... 19218421

(51) Int. Cl.

| | |
|---|---|
| ***C12N 9/20*** | (2006.01) |
| ***C12N 9/18*** | (2006.01) |
| ***C12P 7/62*** | (2022.01) |
| ***C12P 7/6436*** | (2022.01) |
| ***C12P 7/6454*** | (2022.01) |
| ***C12P 19/02*** | (2006.01) |
| ***C12P 19/04*** | (2006.01) |

(52) U.S. Cl.

CPC ................. *C12N 9/20* (2013.01); *C12N 9/18* (2013.01); *C12P 7/62* (2013.01); *C12P 7/6436* (2013.01); *C12P 7/6454* (2013.01); *C12P 19/02* (2013.01); *C12P 19/04* (2013.01)

(58) Field of Classification Search

CPC ................................ C12N 9/20; C12P 7/6436

See application file for complete search history.

(56) References Cited

U.S. PATENT DOCUMENTS

| | | | |
|---|---|---|---|
| 6,320,065 | B1 | 11/2001 | Gruning et al. |
| 2007/0087418 | A1 | 4/2007 | Mazeaud et al. |
| 2009/0088565 | A1 | 4/2009 | Schick et al. |
| 2020/0375862 | A1 | 12/2020 | Brandt et al. |
| 2023/0023141 | A1 | 1/2023 | Von Hof et al. |
| 2023/0055814 | A1 | 2/2023 | Von Hof et al. |

FOREIGN PATENT DOCUMENTS

| | | |
|---|---|---|
| EP | 2902009 | 8/2015 |
| GB | 947830 | 1/1964 |
| GB | 1016885 | 1/1966 |
| GB | 1025028 | 4/1966 |
| JP | 11-346791 | 12/1999 |
| KR | 101939851 | 1/2019 |
| WO | 94/12651 | 6/1994 |
| WO | 2006/117386 | 11/2006 |
| WO | 2021/122971 | 6/2021 |
| WO | 2021/122973 | 6/2021 |
| WO | 2021/190993 | 9/2021 |

OTHER PUBLICATIONS

Castillo et al., "Lipase-catalyzed synthesis of xylitol monoesters: solvent engineering approach", Journal of Biotechnology, vol. 102, Feb. 13, 2003, pp. 251-259.

U.S. Appl. No. 16/857,523, filed Apr. 24, 2020, 2020/0375862, Brandt et al.

Adnani et al., "Chemometric analysis of lipase-catalyzed synthesis of xylitol esters in a solvent-free system", Carbohydrate Research, vol. 346, 2011, pp. 472-479.

Cramer et al., "Controlling the degree of esterification in lipase catalysed synthesis of xylitol fatty acid esters", Enzyme and Microbial Technology, vol. 41, 2007, pp. 346-352.

Ducret et al., "Characterization of Enzymatically Prepared Biosurfactants", Journal of the American Oil Chemists Society, vol. 73, No. 1, 1996, pp. 109-113.

Ducret et al., "Enzymatic Preparation of Biosurfactants from Sugars or Sugar Alcohols and Fatty Acids in Organic Media Under Reduced Pressure", Biotechnology and Bioengineering, vol. 48, No. 3, Nov. 5, 1995, pp. 214-221.

International Search Report dated Apr. 28, 2021 in PCT/EP2020/086737, with English translation, 7 pages.

Written Opinion dated Apr. 28, 2021 in PCT/EP2020/086737, 8 pages.

Elgharbawy et al., "Ionic liquids as a potential solvent for lipase-catalysed reactions: A review", Journal of Molecular Liquids, vol. 251, 2018, pp. 150-166.

Gumel et al., "Lipase mediated synthesis of sugar fatty acid esters", Process Biochemistry, vol. 46, Aug. 4, 2011, pp. 2079-2090.

Office Action received for U.S. Appl. No. 17/757,576, mailed on Jul. 14, 2025, 33 pages.

(Continued)

*Primary Examiner* — Yong D Pak

(74) *Attorney, Agent, or Firm* — Grüneberg Global IP, PLLC

(57) ABSTRACT

Xylitol carboxylates are products of interest in the food and cosmetics industries. A process can be used for the enzymatic preparation of xylitol carboxylates.

20 Claims, No Drawings

(56) References Cited

OTHER PUBLICATIONS

PubChem ID: 119389, Octanoate, https://pubchem.ncbi.nlm.nih.gov/compound/Octanoate, Jul. 2025, 2 pages.
PubChem ID: 13164, Vinyl octanoate, https://pubchem.ncbi.nlm.nih.gov/compoundNinyl-octanoate, Jul. 2025, 2 pages.
PubChem ID: 135191, D-Xylose, https://pubchem.ncbi.nlm.nih.gov/compound/D-Xylose, Jul. 2025, 2 pages.
PubChem ID: 5793, D-Glucose, https://pubchem.ncbi.nlm.nih.gov/compound/D-Glucose, Jul. 2025, 2 pages.
Siebenhaller et al., "Beechwood carbohydrates for enzymatic synthesis of sustainable glycolipids, Bioresources and Bioprocessing", vol. 4, No. 25, Jun. 7, 2017, pp. 1-9.
U.S. Appl. No. 17/757,576, filed Jun. 17, 2022, 2023/0055814, Von Hof et al.

CARBOXYLIC ACID ESTERS OF XYLITOL AND PROCESS FOR ENZYMATICALLY PREPARING SAME

CROSS-REFERENCE TO RELATED APPLICATIONS

This application is the National Stage entry under § 371 of International Application No. PCT/EP2020/086737, filed on Dec. 17, 2020, and which claims the benefit of priority to European Application No. 19218421.6, filed on Dec. 20, 2019. The content of each of these applications is hereby incorporated by reference in its entirety.

BACKGROUND OF THE INVENTION

Field of the Invention

The Invention provides xylitol carboxylates and also a process for the enzymatic preparation of xylitol carboxylates.

Description of Related Art

Xylitol carboxylates are products of interest to the food and cosmetics industries not only on account of their surfactant properties, but also because of the possibility of obtaining them from natural and renewable raw materials.

EP2902009A1 describes the classical chemical esterification of xylitol with fatty acids in the absence of solvents in the presence of catalysts such as p-toluenesulfonic acid (pTSA) at temperatures of up to 200° C. over a period of 8 hours and also the use of the xylitol carboxylates thus obtained as an active ingredient in cosmetic formulations.

A disadvantage of the classical chemical esterification processes is that, under these conditions, xylitol always undergoes an at least partial dehydration/degradation (*Biotechnol. Bioeng.* 1995, 48, 214-221). Three xylitol degradation products that frequently occur under such conditions are the anhydropentitols 1,4-anhydroxylitol, 1,4-anhydroarabitol and 1,4-anhydroxrlitol (J. Carbohydr. Chem. 2004, 23, 4, 169-177 and Adv. Carbohydr. Chem. Biochem., 1983, 41, 27-66). A further disadvantage of the process described in the prior art is the additional process steps such as the use and subsequent removal of activated carbon and terra alba (calcium sulfate) in order to improve the colour and the odour of the products obtained.

Pedersen et al. (*Enzyme Microb. Technol.* 2007, 41, 3, 348-352) describe the enzymatic synthesis of xylitol carboxylates using solvents such as tert-butanol and pyridine at a temperature of 45° C. A disadvantage of this process described in the prior art is that the use of solvents is an obstacle to use in the food or cosmetics sector, in addition to which the requisite removal of the solvents involves additional process steps such as crystallization, filtration or distillation.

Basri et al. (*Carbohydr. Res.* 2011, 346, 472-479) describe the solvent-free esterification of xylitol with both capric acid and caproic acid using a lipase from *Candida antarctica* at max. 70° C. and optimally at 60° C. This process results in product mixtures in which the ratio of esterified primary OH groups to esterified secondary OH groups is always greater than 80:20. A disadvantage of this process described in the prior art is the use of a molecular sieve, which makes implementation on an industrial scale more difficult. A further disadvantage of this process described in the prior art is the use of solvents or solvent mixtures for termination of the reaction, removal of the enzyme and of the molecular sieve. This procedure means an additional process step to remove the solvent used and takes away the advantage of the solvent-free process. A further disadvantage of this process described in the prior art is that tricarboxylic esters of xylitol are obtained as the principal component in a relative proportion of more than 50% in the ester distribution. A further disadvantage of this process described in the prior art is unclear enzyme loading. A further disadvantage of this process described in the prior art is the low conversion rate of only approx. 70% and thus the relatively large amount of fatty acid of approx. 15% remaining in the product mixture, which necessitates a subsequent separation or the fatty acid, where necessary with prior neutralization to avoid unwanted by-products or. In the case or e.g. caproic, caprylic and capric acid, an unpleasant odour. A further disadvantage of this process described in the prior art is the selectivity for long-chain fatty acids.

Tan et al. (*J. Mot. Catal. B-Enzym* 2013, 89, 61-86) describe the solvent-free esterification of xylitol with capric acid using a lipase (*Candida* sp 99-125) at max. 50° C. From the reported analytical data, it can be deduced that the ratio of esterified primary OH groups to esterified secondary OH groups is always greater than 80:20. A disadvantage of this process described in the prior art is the use of very finely milled xylitol (particle size <0.2 mm), which, for implementation on an industrial scale, means an additional process step and the use of special equipment (e.g. Dispermat or special mills). A further disadvantage of this process described in the prior art is long reaction times (>100 hours). A further disadvantage of this process described in the prior art is the removal of by-products at temperatures of >140° C., which has an adverse effect on the colour of the products. A further disadvantage of the process described in the prior art is the use of an enzyme that is not commercially available. A further disadvantage of the process described in the prior art is that the enzyme was not isolated from a wild type.

A further disadvantage of this process described in the prior art is the use of non-Immobilized enzymes, which makes the safety aspects of handling and separation from the product more problematic. A further disadvantage of this process described in the prior at is the poor recyclability of the lipase used. A further disadvantage of this process described in the prior art is the use of a fed-batch process to avoid the high viscosity caused by an excess of xylitol or capric acid. A further disadvantage of this process described in the prior art is the use of a fed-batch process, which requires special measurement and control technology. A further disadvantage of this process described in the prior art is the addition of water, which has to be removed again at the end of the process.

KR101939851B1 describes esters of dehydrated xylitol, thus the above-described by-products of the classic chemical esterification processes for the preparation of xylitol carboxylates, and also the use of these carboxylic esters of anhydroxrlitol as a rheological additive/viscosity regulator in an emulsion. A disadvantage of the anhydroxrlitol carboxylates described in the prior art is their reduced hydrophilicity. A further disadvantage of the anhydroxylitol carboxylates described in the prior art is their dark colour. A further disadvantage of such anhydroxrlitol carboxylates is the poor thickening performance in aqueous surfactant systems.

SUMMARY OF THE INVENTION

The object of the invention was to provide a process for preparing sugar esters and/or sugar alcohol esters that is able to overcome at least one disadvantage of the processes of the prior art.

It has surprisingly been found that the xylitol carboxylates described hereinbelow and the process described hereinbelow are able to achieve the object of the invention.

DETAILED DESCRIPTION OF THE INVENTION

It is an advantage of the present invention that the xylitol carboxylates of the invention are excellent thickeners for aqueous surfactant systems compared to the prior art.

A further advantage is that the xylitol carboxylates of the invention also have excellent colour and very good odour compared to the prior art.

An advantage of the present invention is that only very small amounts of xylitol degradation products or esters of the degradation products are obtained as reaction products.

It is an advantage of the present invention that the process of the invention can be carried out in the absence of a solvent.

A further advantage of the present invention is that the xylitol carboxylates are obtained in a homogeneous reaction mixture, which means that no additional process steps such as extraction, crystallization, filtration or distillation are required.

An advantage of the present invention is that the process can be carried out at elevated temperatures. This results in better miscibility of the co-reactants, while the recyclability of the enzyme used is surprisingly high.

A further advantage of the present invention is that the xylitol carboxylates obtained can be incorporated very readily into formulations, particularly into cosmetic formulations.

The present invention therefore provides a xylitol carboxylate, comprising carboxylic esters of xylitol, carboxylic esters of 1,4-anhydroxrlitol, carboxylic esters of 1,4-anhydroarabitol and carboxylic esters of 1,4-anhydroribitol, wherein the ratio by weight of the xylitol residues present in the xylitol carboxylate to the sum total of all the 1,4-anhydroxrlitol residues, 1,4-anhydroarabitol residues and 1,4-anhydroribitol residues present in the xylitol carboxylate is greater than or equal to 96:4, preferably greater than 97:3, more preferably greater than 98:2, most preferably greater than 99:1, characterized in that the molar ratio of esterified primary hydroxyl groups to esterified secondary hydroxyl groups in the carboxylic esters of xylitol is 80:20 to 20:80, preferably 75:25 to 25:75, even more preferably 70:30 to 30:70, even more preferably from 65:35 to 40:60.

The term "xylitol carboxylates" in the context of the present invention includes a composition that contains at least 30% by weight, preferably at least 40% by weight, more preferably at least 50% by weight, particularly preferably at least 70% by weight, of carboxylic esters of xylitol, based on the total composition. In addition, there may also be present by-products from the respective preparation process, for example carboxylic esters of 1,4-anhydroxrlitol, carboxylic esters of 1,4-anhydroarabitol and carboxylic esters of 1,4-anhydroribitol, and also unreacted reactants.

The term "carboxylic esters of xylitol" in the context of the present invention refers to pure xylitol compounds.

The term "carboxylic esters of 1,4-anhydroxrlitol" in the context of the present invention refers to pure 1,4-anhydroxylitol compounds.

The term "carboxylic esters of 1,4-anhydroxrlitol" in the context of the present invention refers to pure 1,4-anhydroarabitol compounds.

The term "carboxylic esters of 1,4-anhydroxrlitol" in the context of the present invention refers to pure 1,4-anhydroribitol compounds.

This use of terminology is based on the customary nomenclature for polyol esters; these are known to be prone to dehydration during their synthesis, consequently the products are mixtures in composition. Those skilled in the art thus understand the term "sorbitan ester" as meaning a mixture comprising not only esters of 1,4-sorbitan (1,4-anhydrosorbitol) and esters of 1,5-sorbitan (1,5-anhydrosorbitol), but also esters of isosorbide and esters of sorbitol, and also free sorbitol, cf. in this regard also *Food emulsifiers and their applications,* 1997, page 26.

From the expression "xylitol carboxylate, comprising carboxylic esters of xylitol, carboxylic esters of 1,4-anhydroxylitol, carboxylic esters of 1,4-anhydroarabitol and carboxylic esters of 1,4-anhydroribitol, wherein the ratio by weight of the xylitol residues present in the xylitol carboxylate to the sum total of all the 1,4-anhydroxylitol residues, 1,4-anhydroarabitol residues and 1,4-anhydroribitol residues present in the xylitol carboxylate is greater than or equal to 96:4" it is clear and unambiguous that the content in the xylitol carboxylate of the invention of at least one selected from carboxylic esters of 1,4-anhydroxrlitol, carboxylic esters of 1,4-anhydroarabitol and carboxylic esters of 1,4-anhydroribitol must be not equal to 0 (zero), since divisions by 0 are not defined.

Unless otherwise indicated, all stated percentages (%) are percentages by weight.

The ratio by weight of the xylitol residues present in the xylitol carboxylate to the sum total of all the 1,4-anhydroxrlitol residues, 1,4-anhydroarabitol residues and 1,4-anhydroribitol residues present in the xylitol carboxylate of the invention Is determined by high-performance liquid chromatography (HPLC). This method comprises the alkaline hydrolysis of the xylitol carboxylate undergoing analysis, removal of carboxylic acids and analysis of the xylitol and its degradation products 1,4-anhydroxylitol, 1,4-anhydroarabitol and 1,4-anhydroribitol.

For this purpose, an initial charge of 150 mg of the xylitol carboxylate undergoing analysis in 2.00 ml of 1 M aqueous KOH solution is hydrolysed at 95° C. with stirring for 30 min. The reaction solution is then cooled to room temperature and adjusted to pH 2-3 with 2 M aqueous HCl solution.

The carboxylic acids that precipitate out as a result are then extracted with diethyl ether (3×3.00 ml), with removal of the organic supernatant by pipette after each extraction. After the extraction, the aqueous solution is heated to 50° C. with stirring for 20 min, which removes the rest of the ether (boiling point of diethyl ether: 34.6° C.).

The solution obtained above is made up to 10.0 ml with bidistilled $H_2O$ and then diluted 1:10, and an aliquot of the solution is analysed by HPLC. The analysis is carried out under the following conditions:

Column: Aminex HPX-87C column 300×7.8 mm

Eluent: $H_2O$

Injected volume: 10.0 μl

Flow rate: 0.60 ml/min

Column temperature: 50° C.

Detector: G1362A/1260 RID (from Agilent), 35° C.

Run time: 30.0 min

Xylitol and its degradation products are separated by an ion-exchange process.

For the evaluation, the ratio of the peak area of xylitol to the sum total of the peak areas of 1,4-anhydroxylitol, 1,4-anhydroarabitol and 1,4-anhydroribitol is calculated.

Reference substances for the xylitol degradation products are commercially available or can alternatively be obtained by heating xylitol in neat form in the presence of acidic (>140° C.) or basic (>180° C.) catalysts.

The molar ratio of esterified primary hydroxyl groups to esterified secondary hydroxyl groups in the carboxylic esters of xylitol is determined by $^{13}$C-NMR spectroscopy. Samples are prepared by dissolving 50-70 mg of substance in 1 ml of a deuterated solvent to which has been added a relaxation accelerator (chromium(III) acetylacetonate, 1%). DMSO-d6, $CDCl_3$ and methanol-d4 have been found to be suitable solvents, depending on product properties. If the sample does not dissolve completely in one of the solvents, a solvent mixture must be found. The prepared sample solution is transferred to a 5 mm NMR tube and introduced into the NMR spectrometer.

The NMR spectroscopy investigations can in principle be carried out using any commercial NMR instrument. For the present NMR spectroscopy investigations, a Bruker Avance 400 instrument was used. The spectra were recorded with the following parameters:

Temperature: T=295 K, Time delay: D1=2 s, Number of scans: NS=2048, Transmitter frequency offset: O1P=110 ppm, Sweep width: SW=300 ppm, Probe: PA BBI 400 S1 H-BB-D-05-Z.

The resonance signals are recorded against the chemical shift of tetramethylsilane (TMS=0 ppm) as internal standard. Other commercial NMR instruments give comparable results with the same operating parameters. The resonance signals are quantified by determining the area under the respective signal, i.e. the area enclosed by the signal from the baseline. In the present NMR spectroscopy investigations, the spectra were integrated using the 'TOPSPIN' software, version 3.0.

Accurate identification of the esterified primary and esterified secondary hydroxyl groups is achieved primarily by recording a DEPT spectrum. The molar ratio of esterified primary to esterified secondary hydroxyl groups is determined by subtracting the integral value P (group of signals for the esterified primary hydroxyl groups) from integral value C (group of signals for the ester carbonyl groups). This gives an integral value S for the group of signals for the esterified secondary hydroxyl groups, which cannot be determined directly because of overlap with other signals.

P=Integral value of the esterified primary hydroxyl groups [R—$\underline{C}H_2$—OC(O)R groups]

C=Integral value of the ester carbonyl groups

S=C−P=Integral value of the esterified secondary hydroxyl groups [$R_2$—$\underline{C}$H—OC(O)R groups]

The calculated ratio of P to S corresponds to the molar ratio of esterified primary hydroxyl groups to esterified secondary hydroxyl groups in the carboxylic esters of xylitol.

Preference is given in accordance with the invention to xylitol carboxylates characterized in that the carboxylic acid component is derived from a carboxylic acid containing 2 to 34, preferably 4 to 24, more preferably 6 to 22, carbon atoms.

The carboxylic acid component is according to the invention preferably derived from a natural fatty acid or mixtures thereof. According to the invention, preference is given to mixtures of natural fatty acids in which no carboxylic acid chain length has a proportion in the overall chain length distribution of more than 95% by weight, especially more than 99% by weight.

Natural fatty acids can be produced on the basis of naturally occurring vegetable or animal oils and have preferably 6 to 30 carbon atoms, especially 8 to 22 carbon atoms. Natural fatty acids are generally unbranched and usually consist of an even number of carbon atoms. Any double bonds have cis configuration. Examples are: caproic acid, caprylic acid, capric acid, lauric acid, myristic acid, palmitic acid, palmitoleic acid, pelargonic acid (obtainable for example from the ozonolysis or oxidative cleavage of oleic acid), isostearic acid, stearic acid, 12-hydroxystearic acid, dihydroxystearic acid, undecylenic acid (obtainable from the pyrolysis of ricinoleic acid), oleic acid, linoleic acid, linolenic acid, petroselinic acid, elaidic acid, arachic acid, behenic acid, erucic acid, gadoleic acid, eicosapentaenoic acid, docosahexaenoic acid and arachidonic acid.

Preference Is according to the invention given in particular to xylitol carboxylates characterized in that the carboxylic acid component is derived from fatty acid mixtures selected from at least two selected from the group caproic acid, caprylic acid, capric acid, lauric acid, myristic acid, palmitic acid, palmitoleic acid, pelargonic acid (obtainable for example from the ozonolysis or oxidative cleavage of oleic acid), isostearic acid, stearic acid, 12-hydroxystearic acid, dihydroxystearic acid, undecylenic acid (obtainable for example from the pyrolysis of ricinoleic acid), oleic acid, linoleic acid, linolenic acid, petroselinic acid, elaidic acid, arachic acid, behenic acid, erucic acid, gadoleic acid, eicosapentaenoic acid, docosahexaenoic acid and arachidonic acid.

Preference Is given in accordance with the invention to xylitol carboxylates characterized in that the average degree of esterification of the carboxylic esters of xylitol present is from 1.0 to 4.0, preferably from 1.0 to 3.0, more preferably from 1.1 to 2.7, particularly preferably from 1.3 to 2.6. Preference Is according to the invention alternatively given to xylitol carboxylates characterized in that the average degree of esterification of the carboxylic esters of xylitol present is from 2.7 to 4.0.

The average degree of esterification of the carboxylic esters of xylitol present in the xylitol carboxylate of the invention is determined for example by first determining, via GC or HPLC in a sample of the xylitol carboxylate concerned, the content of free xylitol and of its degradation products 1,4-anhydroxylitol, 1,4-anhydroarabitol and 1,4-anhydroribitol. The saponification value, acid value and content of free and neutralized fatty acids (for example via GC as described hereinbelow under "Determination of the content of free carboxylic acid") must additionally be determined. The determination of the carboxylic acid composition after alkaline saponification gives an average molar mass of the carboxylic acid residues present in the xylitol carboxylate.

This value can then be used to calculate the average degree of esterification.

Preference is given in accordance with the invention to a xylitol carboxylate characterized in that the carboxylic esters of xylitol present comprise monoesters of xylitol, diesters of xylitol and triesters of xylitol, wherein the triesters of xylitol are present preferably in an amount, based on all carboxylic esters of xylitol present, of from 10% to 50% by weight, preferably from 15% by weight to 45% by weight, more preferably from 20% by weight to 40% by weight. In this connection, it is according to the invention further preferable that the carboxylic esters of xylitol present comprise monoesters of xylitol, diesters of xylitol, triesters of xylitol and tetraesters of xylitol.

Preference is given in accordance with the invention to a xylitol carboxylate characterized in that it contains 0.05% to 40% by weight, preferably 0.2% to 25% by weight, more preferably 0.5% to 10% by weight, of free xylitol, the percentages by weight being based on the total xylitol carboxylates.

For determination of the xylitol present in the xylitol carboxylates of the invention by GC, a portion of the sample is dissolved in pyridine:chloroform (4:1). 0.25 ml of this solution is mixed with 0.5 ml of MSTFA [N-methyl-N-(trimethylsilyl)trifluoroacetamide] and 0.5 ml of a mixture of N-trimethylsilylimidazole and pyridine (11:39).

The alcohols are quantitatively converted into their trimethylsilyl ethers by reaction at 80° C. (30 minutes) and then analysed by GC/FID.

This is performed in a gas chromatograph equipped with a split/splitless injector, a capillary column and a flame ionization detector, under the following conditions:

Injector: 290° C., split 30 ml

Injected volume: 1 μl

Column: 50 m*0.32 mm HP5 1.05 μm

Carrier gas: Hydrogen, constant flow, 2 ml/min

Temperature program: 100° C. to 140° C. at 10° C./min, then 140° C. to 300° C. at 5° C./min, then conditioning at 300° C. for 5 minutes.

Detector: FID at 310° C.

Hydrogen 30 m/min

Air 400 ml/min

Make-up gas 12 m/min

The xylitol is separated and its proportion by mass determined by an internal standard method. For this, the GC system is calibrated by analysing mixtures of xylitol and of the internal standard of known composition.

Preference is given in accordance with the invention to a xylitol carboxylate characterized in that it contains less than 25% by weight, preferably from 0.01% by weight to 20% by weight, more preferably from 0.05% by weight to 10% by weight, of at least one free carboxylic acid, the percentages by weight being based on the total xylitol carboxylates.

The at least one free carboxylic acid may be present in protonated or neutralized form.

To determine the content of free carboxylic acid in the xylitol carboxylates of the invention, the acid value is first determined. From the acid value and the molecular weight of the fatty acid concerned, it is possible to determine the proportion by weight.

Suitable methods for determining the acid value are in particular those according to DGF C-V 2, DIN EN ISO 2114, Ph. Eur. 2.5.1, ISO 3682 and ASTM D 974.

It is known to those skilled in the art that, where there is a mixture of carboxylic acids, a GC analysis can also additionally be carried out after saponification of the xylitol carboxylate, in order to determine an average molecular weight of the carboxylic acid mixture present:

For this, 0.6 g of the xylitol carboxylate of the invention is boiled under reflux in 25 ml of 0.5 M ethanolic KOH solution for 4 hours. The pH is then adjusted to 2-3 with sulfuric acid and the liberated carboxylic acids are separated by extracting with three portions or petroleum ether. The combined extracts are concentrated to approx. 10 ml by evaporation.

Suitable methods for determining the fatty acid distribution are in particular those according to DGF C VI 11a, DGF C-VI 10 a and GAT ring test 7/99.

A 0.5 ml aliquot of the petroleum ether extract obtained as described above is mixed in an autosampler vial with 0.5 ml of MTBE and 1 ml of trimethylanilinium hydroxide (0.2 M in methanol) and analysed by GC. This is performed in a gas chromatograph equipped with a split/splitless injector, a capillary column and a flame ionization detector, under the following conditions:

Injector: 290° C., split 30 ml

Injected volume: 1 μl

Column: 30 m*0.32 mm HP1 0.25 μm

Carrier gas: Helium, head pressure 70 kPa

Temperature program: 80° C. to 300° C. at 8° C./min, then conditioning at 300° C. for 20 minutes.

Detector: FID at 320° C.

Hydrogen 35 ml/min

Air 240 m/min

Make-up gas 12 m/min

The carboxylic acids are separated in the form of their methyl esters according to the length of their carbon chain. By evaluating the peak areas it is possible to determine the mass ratio of these carboxylic acid methyl esters to one another and from this—via their respective molecular weights—their molar ratio, which corresponds to the molar ratio of the associated carboxylic acids. It is in addition possible to determine an average molecular weight of this fatty acid mixture:

$$a_i = \frac{A_i}{\sum_i A_i} \cdot 100$$

where $a_i$=Normalized proportion by mass of carboxylic acid methyl ester i in the mixture of all carboxylic acid methyl esters [%].

$A_i$=Peak area of carboxylic acid methyl ester i in the GC chromatogram [%].

$$n_i = \frac{a_i}{(M_i + 14)}$$

where $n_i$=Molar amount [mol] of carboxylic acid methyl ester i in 100 g of the mixture of carboxylic acid methyl esters; from this, the ratios of the individual $n_i$ values to one another are obtained, which correspond to the ratios of the molar amounts of the associated carboxylic acids in the xylitol carboxylate; thus it is possible for the total molar amount $n_s$ [mol] of carboxylic acids in 1 g of xylitol carboxylate, as obtained from the saponification value (see below), to be split into its components according to said ratios.

$M_i$=Molecular weight of the carboxylic acid corresponding to methyl ester i [g/mol].

$$\overline{M_s} = \sum_i \left( \frac{n_i}{\sum_i n_i} \cdot M_i \right)$$

where $\overline{M_s}$=Average molecular weight of the mixture of carboxylic acids.

$n_i$=Molar amount [mol] of carboxylic acid methyl ester i in 100 g of the mixture of carboxylic acid methyl esters.

$M_i$=Molecular weight of carboxylic acid i [g/mol].

Preference is given in accordance with the invention to a xylitol carboxylate characterized in that the total monoester component of the carboxylic ester of xylitol contains from 5% by weight to 25% by weight, preferably from 7% by weight to 15% by weight, more preferably from 9% by weight to 13% by weight, of secondary ester regioisomers.

Preference is given in accordance with the invention to a xylitol carboxylate characterized in that the total monoester component of the carboxylic ester of xylitol and the total diester component of the carboxylic ester of xylitol each comprise at least two regioisomers.

Preference is given in accordance with the invention to a xylitol carboxylate characterized in that the total diester component of the carboxylic ester of xylitol contains from 25% by weight to 45% by weight, preferably from 28% by weight to 39% by weight, more preferably from 30% by weight to 37% by weight, of regioisomers in which at least one secondary hydroxyl group has been esterified.

The determination of the content of secondary ester regioisomer in the total monoester component of the carboxylic ester of xylitol of the invention, the determination of the content of triester species based on the sum total of all carboxylic esters of xylitol that are present, and the determination of the content of regioisomers in the total diester component in which at least one secondary hydroxyl group has been esterified can be performed by gas chromatography, optionally coupled with mass spectrometry (GC-FID and GC-MS):

10 mg of a sample of the corresponding xylitol carboxylates is first dissolved in 1.5 ml of trichloromethane and 0.15 ml of N-methyl-N-(trimethylsilyl)trifluoroacetamide (MSTFA) Is then added. The derivatization is carried out at 80° C. for 30 minutes. A sample of the clear solution thus obtained is analysed by GC-FID and GC-MS. The parameters of the analysis method are as follows:

Gas chromatograph: Agilent MSD 7890

Column: Agilent HP-5 (50 m, 0.32 mm, 0.5 μm),

Flow rate: Constant 2 ml/min with hydrogen (GC-MS: helium)

Thermal equilibration at 80° C., 8° C./min; 300° C. 30 min, Injector 1 μl, split 1:20, detector at 310° C.

Detector: FID, 310° C./GC-MS scan 35-450 d

In the GC-FID analysis, the esters present in the sample are separated according to their total chain length. The ratios of the individual ester species to one another are determined via the respective area percentage of the GC-FID peak. The peaks are identified/assigned to the individual ester species via GC-MS, where necessary also via a comparison with retention times of separately prepared and isolated standards, for example for mono- and diesters esterified exclusively at primary hydroxyl groups.

This method can likewise be used to record the content of free protonated and also free neutralized carboxylic acids, since these are likewise derivatized.

The invention further provides a process for the enzymatic preparation of a xylitol carboxylate, preferably of a xylitol carboxylate of the invention, comprising the process steps of A) providing xylitol and at least one acyl group donor, preferably fatty acid acyl group donor, selected in particular from fatty acid esters and fatty acids, particularly preferably fatty acids, B) reacting xylitol with the at least one acyl group donor in the presence of a lipase at a temperature of from 75° C. to 110° C., preferably from 77° C. to 100° C., even more preferably 80° C. to 95° C., to give a xylitol carboxylate, and optionally C) purifying the xylitol carboxylate.

It is in accordance with the invention possible for any acyl group donors to be used in accordance with the invention. These include for example carboxylic esters or carboxylic acids themselves, and also mixtures thereof.

Carboxylic esters used with preference in accordance with the invention as acyl group donor are selected from esters based on alkanols and polyols having up to 8 carbon atoms, particularly preferably having up to 3 carbon atoms, very particularly preferably glycerol esters.

Carboxylic esters used with particular preference in accordance with the invention as acyl group donor are selected from triglycerides, especially natural fats and oils, particularly preferably selected from the group comprising, preferably consisting of, coconut fat, palm kernel oil, olive oil, palm oil, argan oil, castor oil, linseed oil, babassu oil, rapeseed oil, algal oils, sesame oil, soya oil, avocado oil, jojoba oil, safflower oil, almond oil, cottonseed oil, shea butter, sunflower oil, cupuaçu butter and oils having a high proportion of polyunsaturated fatty acids (PUFAs). Preference may likewise be given to using sorbitan esters, monoglycerides and diglycerides, particularly ones containing the acyl groups described hereinbelow.

It is in accordance with the invention particularly preferable that the acyl group donor is selected from fatty acid acyl group donors that in particular provide an acyl group selected from the group of acyl groups of natural fatty acids. Preferred fatty acids in this connection are those mentioned above in connection with the xylitol carboxylate or the invention, preferably fatty acids forming the carboxylic acid component, with an identical degree of preference.

Preference is given in accordance with the invention to using as acyl group donor carboxylic acids, especially fatty acids, wherein the fatty acids specifically mentioned above in connection with the xylitol carboxylate of the invention are preferably used with an identical degree of preference.

Preference according to the invention is alternatively given to using as acyl group donor mixtures of fatty acids with glycerol fatty acid esters, wherein the fatty acids specifically mentioned above in connection with the xylitol carboxylate of the invention are preferably used with an identical degree of preference both in the fatty acids and in the glycerol fatty acid components.

The employed mixture of fatty acid with glycerol fatty acid ester preferably has a weight ratio of fatty acid to glycerol fatty acid ester of from 80:20 to 99:1, preferably from 90:10 to 99:1, more preferably from 95:5 to 99:1.

A process preferred in accordance with the invention is characterized in that the xylitol and the at least one acyl group donor make up at least 80% by weight, preferably at least 90% by weight, more preferably at least 95% by weight, based on the overall reaction mixture at the start of process step B).

Since the overall reaction mixture in this context consists largely of the reactants, i.e. xylitol and acyl group donor, only very little solvent—If any—can be present in the overall reaction mixture. On the basis of the above, it is clear that the acyl group donor is not covered by the term “solvent” in the process of the invention.

Possible solvents would be for example ketones, for example methyl isobutyl ketone or cyclohexanone, sterically hindered secondary alcohols such as 2-butyl-1-octanol, methylcyclohexanols, 1-methoxy-2-propanol, butane-2,3-diol, 2-octanol, diacetone alcohol, 2-methyl-2-butanol, and ethers such as 1,4-dioxane, tetrahydrofuran and Varonic APM.

Based on the overall reaction mixture, solvents are present in a maximum total amount of less than 20% by weight, preferably less than 10% by weight, especially less than 5% by weight. The expression "is present in a maximum amount of less than X % by weight" can be equated with "has a content of less than X % by weight".

Particular preference is given to carrying out the process of the invention in the absence of solvent.

A process that is preferred in accordance with the invention is characterized in that the molar ratio of xylitol provided to acyl groups present in all acyl group donors provided is within a range from 1.00:0.30 to 1.00:5.00, preferably from 1.00:0.70 to 1.00:3.00, particularly preferably from 1.00:1.00 to 1.00:2.25, alternatively particularly preferably from 1.00:2.3 to 1.00:4.50.

A process that is preferred in accordance with the invention is characterized in that process step A) comprises blending the xylitol and the at least one acyl group donor for at least ten minutes, preferably 30 minutes, even more preferably 60 minutes, wherein the blending is preferably carried out within a temperature range from 80° C. to 120° C., preferably from 90° C. to 120° C., even more preferably from 95° C. to 120° C., even more preferably from 100° C. to 120° C.

Lipases used with preference in accordance with the invention in process step B) are present immobilized on a solid support.

Lipases used with preference in accordance with the invention in process step B) are lipases selected from the group comprising the lipase from *Thermomyces lanuginosus* (accession number 059952), lipases A and B (accession number P41365) from *Candida antarctica* and the lipase from *Mucor miehel* (accession number P19515), the lipase from *Humicola* sp. (accession number 059952), the lipase from *Rhizomucor javanicus* (accession number S32492), the lipase from *Rhizopus oryzae* (accession number P61872), the lipases from *Candida rugosa* (accession number P20261, P32948, P32947, P3294 and P32949), the lipase from *Rhizopus niveus* (accession number P61871), the lipase from *Penicillium camemberti* (accession number P25234), the lipases from *Aspergillus niger* (ABG73613, ABG73814 and ABG37906) and the lipase from *Penicillium cyclopium* (accession number P61869), particular preference being given to lipases A and B (accession number P41365) from *Candida antarctica*, and their respective at least 60%, with preference at least 80%, preferably at least 90% and especially preferably at least 95%, 98% or 99%, homologues at the amino acid level.

The accession numbers listed in the context of the present invention correspond to the NCBI ProteinBank database entries with a date of 1 Jan. 2017; the version number of the entry is in the present context generally identified by ".digit", for example ".1".

Enzymes that are homologous at the amino acid level preferably exhibit, by comparison with the reference sequence, at least 50%, especially at least 90%, of the enzyme activity in propyl laurate units as defined in the context or the present invention.

To determine the enzyme activity in PLU (propyl laurate units), 1-propanol and lauric acid are mixed homogeneously in an equimolar ratio at 60° C. The reaction is started with addition of enzyme and the reaction time is measured. Samples are taken from the reaction mixture at intervals and the content of converted lauric acid is determined by titration with potassium hydroxide solution. The enzyme activity in PLU results from the rate at which 1 g of the enzyme concerned synthesizes 1 μmol of propyl laurate per minute at 60° C.; cf. In this regard also US20070087418, in particular [0185].

Commercial examples, and lipases that are likewise used with preference in processes according to the invention, are the commercial products Lipozyme™ TL IM, Novozym™ 435, Lipozyme™ IM 20, Lipase SP382, Lipase SP525, Lipase SP523, (all commercial products from Novozymes IM A/S, Bagsvaerd, Denmark), Chirazyme L2, Chirazyme L5, Chirazyme L8, Chirazyme L9 (all commercial products from Roche Molecular Biochemicals, Mannheim, Germany), CALB Immo Plus™ from Purolite™, and Lipase M "Amano IM" Lipase F-AP 15 "Amano™", Lipase AY "Amano™", Lipase N "Amano™", Lipase R "Amano™", Lipase A "Amano™", Lipase D "Amano™", Lipase G "Amano" (all commercial products from Amano™, Japan).

"Homology at the amino acid level" is for the purposes of the present invention understood as meaning "amino acid identity", which can be determined with the aid of known methods. In general, use is made or special computer programs with algorithms taking into account specific requirements. Preferred methods for determining the identity first generate the greatest alignment between the sequences to be compared. Computer programs for determining the identity include, but are not limited to, the GCG program package including GAP (Deveroy, J. et al., Nucleic Acid Research 12 (1984), page 387, Genetics Computer Group University of Wisconsin, Medicine (WI), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbook, Altschul S. et al., NCBI NLM NIH Bethesda N. Dak. 22894; Altschul S. et al., above).

Those skilled in the art are aware that various computer programs are available for the calculation of similarity or identity between two nucleotide or amino acid sequences. For instance, the percentage identity between two amino acid sequences can be determined for example by the algorithm developed by Needleman and Wunsch (J. Mol. Biol. (48): 444-453 (1970)), which has been integrated into the GAP program in the GCG software package (available at http://www.gcg.com), using either a Blossom 62 matrix or a PAM250 matrix, a gap weight of 16, 14, 12, 10, 8, 6 or 4 and a length weight of 1, 2, 3, 4, 5 or 8. Those skilled in the art will recognize that the use of different parameters will lead to slightly different results, but that the percentage identity between two amino acid sequences overall will not be significantly different. The Blossom 62 matrix is typically employed, using the default settings (gap weight: 12, length weight: 1).

In the context of the present invention, an identity of 60% according to the above algorithm means 60% homology. The same applies to higher identities.

In process step B), preference is given in accordance with the invention to using 500 PLU to 2000 PLU, preferably from 200 PLU to 1500 PLU, more preferably from 25 PLU to 1250 PLU, of lipase per gram of xylitol to be converted.

Process step B) is according to the invention preferably carried out at a pressure of less than 1 bar, preferably less than 0.5 bar and more preferably less than 0.1 bar.

Process step B) Is according to the invention alternatively preferably carried out in a bubble column reactor, with at least one inert gas being passed through the reaction mixture; this gas is preferably selected from the group comprising, preferably consisting of, nitrogen and argon. In this connection, it is preferable in accordance with the invention for the gas stream to be 1 to 80 kg/h, preferably 5 to 25 kg/h, even more preferably 10 to 14 kg/h.

Process step B) is in accordance with the invention preferably characterized in that process step B) is ended no later than 180 hours, preferably 120 hours, more preferably 100 hours, after the lipase has been added.

A process that is preferred in accordance with the invention Is characterized in that by-products formed in process step B), for example water when the acyl group donor used is an acid and the corresponding alcohol when the acyl group donor used is an ester, are removed.

This is possible for example by distillation.

Process step C) of the process of the invention comprises the purification of the xylitol carboxylate. All methodologies that allow the xylitol carboxylate to be obtained in higher concentration can be employed for this purpose.

It is in accordance with the invention preferable that the process of the invention includes the removal, in process step C), of the lipase used in the process of the invention.

When the lipase is present immobilized on a support, it is according to the invention preferable that the lipase is removed by filtration through a filter, especially a bag filter, having a fineness of from 0.1μ to 1250μ, preferably from 0.5μ to 100μ.

The process of the present invention is according to the invention preferably characterized in that it does not involve the use of any molecular sieve.

The process of the present invention is according to the invention preferably characterized in that the substrates are not immobilized on solid supports such as silica.

The present invention further provides the xylitol carboxylates obtainable by the process of the invention.

The present invention further provides for the use of the inventive xylitol carboxylates and/or of the xylitol carboxylates obtainable by the process of the invention as viscosity regulator, care active ingredient, foam booster or solubilizer, antimicrobial agent, antistat, binder, corrosion inhibitor, dispersant, emulsifier, film former, humectant, opacifier, oral care agent, preservative, skincare agent, hydrophilic emollient, foam stabilizer and nonionic surfactant, preferably as viscosity regulator, emulsifier, antimicrobial agent and hydrophilic emollient, particularly preferably as viscosity regulator, especially as thickener, especially in cleansing or care formulations.

The examples that follow describe the present invention by way of example, without any intention to limit the invention, the scope of application of which is apparent from the entirety of the description, to the embodiments specified in the examples.

EXAMPLES

Various xylitol carboxylates were synthesized as described hereinbelow.

Method for Determining Colour Numbers

An aliquot (approx. 10 g. so that the cuvette is sufficiently filled), was measured in a Lico 690 spectral colorimeter at room temperature or 90° C. in an 11 mm round cuvette and the colour numbers indicated in each case were recorded.

Example 1: Enzymatic Esterification of Xylitol with 2.00 Equiv. of Caprylic Acid (Inventive)

A mixture of xylitol (60.0 g, 0.394 mol, 1.00 equiv.) and caprylic acid (acid value=389 mg KOH/g, >98%, 113.70 g, 0.788 mol, 2.00 equiv.) was heated to 80° C. with stirring and while passing $N_2$ through, and after 1 h immobilized *Candida antarctica* lipase B enzyme (5.21 g; Purolite D5619, corresponding to 45110 PLU) was added. The mixture was stirred at 80° C. and 15 mbar for 24 h, during which time the water that formed was continuously distilled off. The mixture was then filtered at 80° C. through a Büchner funnel with black ribbon filter to remove the enzyme. The product 25 obtained was homogeneous in the melt, colourless and had an acid value of 1.2 mg KOH/g. The content of triesters based on the sum total of all carboxylic esters of xylitol present was 27% by weight, determined via the area-% values of the GC-FID peaks.

Example 2: Enzymatic Esterification of Xylitol with 2.00 Equiv. Of Caprylic/Capric Acid (Inventive)

A mixture of xylitol (70.8 g, 0.465 mol, 1.00 equiv.) and a caprylic/capric acid mixture (acid value=382 mg KOH/g, mixing ratio of caprylic acid to capric acid 60:40, 146.0 g, 0.930 mol, 2.00 equiv.) was heated to 90° C. for 1 h with stirring and while passing $N_2$ through and, after cooling to 85° C., immobilized *Candida antarctica* lipase B enzyme (6.50 g; Purolite D5819, corresponding to 56280 PLU) was added. The mixture was stirred at 85° C. and 50 mbar for 24 h, during which time the water that formed was continuously distilled off. The mixture was then filtered at 80° C. through a Buchner funnel with black ribbon filter to remove the enzyme. The product obtained was homogeneous in the melt, colourless and had an acid value of 2.7 mg KOH/g. The content of triesters based on the sum total of all carboxylic esters of xylitol present was 28% by weight, determined via the area-% values of the GC-FID peaks.

Example 3: Enzymatic Esterification of Xylitol with 1.80 Equiv. Of Capryllic/Capric Acid (Inventive)

A mixture of xylitol (75.7 g, 0.497 mol, 1.00 equiv.) and a caprylic/capric acid mixture (acid value=362 mg KOH/g, mixing ratio of caprylic acid to capric acid 60:40, 140.5 g, 0.895 mol, 1.80 equiv.) was heated to 90° C. for 1 h with stirring and while passing $N_2$ through and, after cooling to 85° C., immobilized *Candida antarctica* lipase B enzyme (6.48 g: Purolite D5819, corresponding to 58106 PLU) was added. The mixture was stirred at 85° C. and 50 mbar for 24 h. during which time the water that formed was continuously distilled off. The mixture was then filtered at 80° C. through a Büchner funnel with black ribbon filter to remove the enzyme. The product obtained was homogeneous in the melt, colourless and had an acid value of 1.5 mg KOH/g. The content of triesters based on the sum total of all carboxylic esters of xylitol present was 25% by weight, determined via the area-% values of the GC-FID peaks.

Example 4: Enzymatic Esterification of Xylitol with 2.00 Equiv. Of Stearic Acid (Inventive)

A mixture of xylitol (40.00 g, 0.263 mol, 1.00 equiv.) and stearic acid (acid value=198 mg KOH/g, >92%, 148.18 g, 0.526 mol, 2.00 equiv.) was heated to 90° C. with stirring and while passing $N_2$ through, and after 1 h immobilized *Candida antarctica* lipase B enzyme (5.65 g; Purolite D5619, corresponding to 48919 PLU) was added. The mixture was stirred at 90° C. and 15 mbar for 24 h, during which time the water that formed was continuously distilled off. The mixture was then filtered at 80° C. through a Büchner funnel with black ribbon filter to remove the enzyme. The product obtained was homogeneous in the melt, clear, pale yellow and had an acid value of 1.3 mg KOH/g. The content of triesters based on the sum total of all carboxylic esters of xylitol present was 35% by weight, determined via the area-% values of the GC-FID peaks.

Example 5: Enzymatic Esterification of Xylitol with 2.00 Equiv. Of Oleic Acid (Inventive)

A mixture of xylitol (40.00 g, 0.263 mol, 1.00 equiv.) and oleic acid (acid value=200 mg KOH/g, iodine value=92.3 g $I_2$/100 g, 147.5 g, 0.526 mol, 2.00 equiv.) was heated to 90° C. with stirring and while passing $N_2$ through and, after 1 h, immobilized *Candida antarctica* lipase B enzyme (5.65 g; Purolite D5619, corresponding to 48919 PLU) was added. The mixture was stirred at 80° C. and 15 mbar for 24 h, during which time the water that formed was continuously distilled off. The mixture was then filtered at 80° C. through a Büchner funnel with black ribbon filter to remove the enzyme. The product obtained was homogeneous in the melt, clear, yellowish and had an acid value of 1.1 mg KOH/g. The content of triesters based on the sum total of all carboxylic esters of xylitol present was 34% by weight, determined via the area-% values or the GC-FID peaks.

Example 6: Xylidyl Caprate/Caprylate (Noninventive)

A commercial product, GiO™-103 from GiOrbis Laboratories served here as the sample.

Example 7: Esterification of Xylitol with 2.00 Equiv. Of Caprylic Acid According to KR101939851 (Noninventive)

The esterification of xylitol with fatty acids in the presence of acid catalysts at high temperatures is described for example in KR101939851 or EP2902009A1:

A mixture of xylitol (76.1 g, 0.500 mol, 1.00 equiv.) and caprylic acid (acid value=389 mg KOH/g, >98%, 144.2 g, 1.00 mol, 2.00 equiv.) was, after addition of para-toluenesulfonic acid (0.29 g, 0.2% based on caprylic acid), heated to 200° C. while stirring and passing $N_2$ through. The mixture was then stirred at this temperature for 8 h, during which time the water that formed was continuously distilled off, until an acid value of 0.7 mg KOH/g was reached. The product obtained was yellow to brown and had a Gardner colour number of 6.4.

Example 8: Enzymatic Esterication of Xylitol with 2.00 Equiv. of Caprylic Acid at Low Temperature (Noninventive)

A mixture of xylitol (75.2 g, 0.494 mol, 1.00 equiv.), caprylic acid (acid value=389 mg KOH/g, >98%, 142.6 g, 0.989 mol, 2.00 equiv.), was reacted enzymatically as described in Basri et al. (*Carbohydr. Res.* 2011, 346, 472-479) at 60° C. for 29 h while stirring and passing $N_2$ through. The product obtained was inhomogeneous in the melt (i.e. it formed two phases) and had an acid value of approx. 360 mg KOH/g.

Table 1 compares the parameters determined for the inventive and noninventive examples.

TABLE 1

| Ex. | Ratio Xylitol:degradation products | NMR (prim.:sec.) | Free xylitol by GC [%] | Acid value | Gardner colour number |
|---|---|---|---|---|---|
| 1 * | >99:1 | 51:49 | 1.9 | 1.2 | 0 |
| 2 * | >99:1 | 53:47 | 1.6 | 2.7 | 0 |
| 3 * | >99:1 | 54:46 | 4.4 | 1.5 | 0 |
| 4 * | >99:1 | 57:43 | 0.9 | 1.3 | 0 |
| 5 * | >99:1 | 55:45 | 1.3 | 1.1 | 1 |
| 6 | 95:5 | 67:33 | 10 | 3 | 7 |
| 7 | 1:99 | Method not applicable | <0.05 | 0.7 | 6.4 |
| 8 | >99:1 | 81:19 | 0.3 | (360) | 0 |

inventive examples are marked with an asterisk

Example 9: Thickening Performance in a Cosmetic Formulation

The thickening effect of inventive examples 1, 2 and 3 was evaluated in comparison with noninventive thickeners. For this purpose, a cosmetic formulation consisting of 9% SLES, 3% Cocamidopropyl Betaine and 0.7% NaCl in water was produced. The pH of this formulation was adjusted to 5.2 with citric acid. Into this formulation was in each case incorporated 1.1% of the example substances mentioned above by stirring at 60° C. for 30 min, and the viscosities were measured using a Brookfield viscometer (spindle 62, 30 rpm) at 22° C. The results of the viscosity measurements are shown in Table 2.

TABLE 2

Viscosity of the example formulation containing 1.1% thickener

| Example | | Viscosity [mPa*s] |
|---|---|---|
| 1 | inventive | 7733 |
| 2 | inventive | 7200 |
| 3 | inventive | 7776 |
| 6 | noninventive | 5995 |
| 7 | noninventive | 1313 |
| 8 | noninventive | 3968 |

The results shown in Table 2 show that the formulations obtained in inventive examples 1, 2 and 3 have higher viscosity than in the noninventive examples.

Formulation Examples

Recipes 1a, 1b and 1c: Antiperspirant/Deodorant Formulations Containing Aluminium Salts

| Recipe | 1a | 1b | 1c |
|---|---|---|---|
| Composition from example 4 | 3.2% | 3.2% | 3.2% |
| C18-C22 Hydroxyalkyl Hydroxypropyl Guar (ESAFLOR HM 22, Lamberti S.p.A.) | 0.2% | | |

-continued

| Recipe | 1a | 1b | 1c |
|---|---|---|---|
| Hydroxypropyl Guar (ESAFLOR HDR, Lamberti S.p.A.) | | 0.2% | 0.2% |
| Isoamyl Cocoate (TEGOSOFT ® AC, Evonik Operations GmbH) | 5.4% | 5.4% | 5.4% |
| Water | to 100% | to 100% | to 100% |
| Aluminum Chlorohydrate (50% aq.; Locron LIC, Clariant AG) | 20.0% | 20.0% | 20.0% |
| Methylisothiazolinone, Methylparaben, Ethylparaben; Dipropylene Glycol (Microcare MEM, Thor) | 0.8% | 0.8% | |
| Undecylenamidopropyltrimonium Methosulfate; Aqua; Propylene Glycol (dermosoft ® UTM, Evonik Dr. Straetmans GmbH) | | | 1.0% |

Recipes 2a, 2b and 2c: Aluminium-Free Deodorant Formulation without Antiperspirant Active Ingredients

| Recipe | 2a | 2b | 2c |
|---|---|---|---|
| Composition from example 4 | 3.2% | 3.2% | 3.2% |
| Hydroxypropyl Guar (ESAFLOR HDR, Lamberti S.p.A.) | 0.15% | | |
| C18-C22 Hydroxyalkyl Hydroxypropyl Guar (ESAFLOR HM 22, Lamberti S.p.A.) | | 0.15% | 0.15% |
| Polyglycery-3 Caprylate (TEGO ® Cosmo P 813, Evonik Operations GmbH) | 0.5% | 0.5% | 0.5% |
| Zinc Ricinoleate (TEGODEO ® PY 88 G, Evonik Operations GmbH) | 1.0% | 1.0% | 1.0% |
| Caprylic/Capric Triglyceride (TEGOSOFT ® CT, Evonik Operations GmbH) | 5.65% | 5.65% | 5.65% |
| Water | to 100% | to 100% | to 100% |
| Glycerin | 3.0% | 3.0% | 3.0% |
| Benzyl Alcohol, Benzoic Acid, Sorbic Acid (Rokonsal BSB-N, Ashland Specialty Ingredients) | 1.0% | 1.0% | 1.0% |
| Citric Acid (50% aq.) | q.s. | q.s. | q.s. |
| Pentylene Glycol (dermosoft ® Pentiol eco, Evonik Dr. Straetmans GmbH) | | | 4.0 |

Recipes 3a, 3b and 3c: O/W Deodorant Emulsion Containing Potassium Alum

| Recipe | 3a | 3b | 3c |
|---|---|---|---|
| Composition from example 4 | 4.8% | 4.8% | 4.8% |
| C18-C22 Hydroxyalkyl Hydroxypropyl Guar (ESAFLOR HM 22, Lamberti S.p.A.) | 0.25% | | |
| Hydroxypropyl Guar (ESAFLOR HDR, Lamberti S.p.A.) | | 0.25% | 0.25% |
| Isopropyl Palmitate (TEGOSOFT ® P, Evonik Operations GmbH) | 5.0% | 5.0% | 5.0% |
| Water | to 100% | to 100% | to 100% |
| Glycerin | 3.0% | 3.0% | 3.0% |
| Potassium alum | 5.0% | 5.0% | 5.0% |
| Methylisothiazolinone, Methylparaben, Ethylparaben; Dipropylene Glycol (Microcare MEM, Thor) | 0.8% | 0.8% | |
| Pentylene Glycol (dermosoft ® Pentiol eco, Evonik Dr. Straetmans GmbH | | | 3.5% |

Recipes 4a and 4b: Antiperspirant/Deodorant Lotion

| Recipe | 4a | 4b |
|---|---|---|
| Composition from example 4 | 3.0% | 3.0% |
| Diethylhexyl Carbonate (TEGOSOFT ® DEC, Evonik Operations GmbH) | 3.0% | 3.0% |
| PPG-14 Butyl Ether (TEGOSOFT ® PBE, Evonik Operations GmbH) | 3.0% | 3.0% |
| Polyglyceryl-3 Caprylate (TEGO ® Cosmo P813, Evonik Operations GmbH) | 0.5% | 0.5% |

-continued

| Recipe | 4a | 4b |
|---|---|---|
| Demineralized water | to 100% | to 100% |
| Hydroxyethylcellulose (Natrosol 250 HHR, Ashland Specialty Chemicals) | 1.0% | 1.0% |
| Aluminum Chlorohydrate (50%) (Reach 501L, Reheis) | 15.0% | 15.0% |
| Methylisothiazolinone, Methylparaben, Ethylparaben; Dipropylene Glycol (Microcare MEM, Thor) | 0.8% | 3.0% |
| 1,2-Hexanediol (dermosoft ® Hexiol, Evonik Dr. Straetmans GmbH) | | 2.8% |

Recipe 5a and 5b 5c: Antiperspirant/Deodorant Creams

| Recipe | 5a | 5b | 5c |
|---|---|---|---|
| Composition from example 4 | 3.0% | 2.5% | 2.5% |
| Sodium Cetearyl Sulfate (Lanette E, BASF SE) | | 0.5% | 0.5% |
| Glyceryl Stearate | 1.0% | 1.0% | 1.0% |
| Stearyl Alcohol | 1.0% | 1.0% | 1.0% |
| PPG-15 Stearyl Ether | 5.0% | 5.0% | 5.0% |
| Isoamyl Cocoate (TEGOSOFT ® AC, Evonik Operations GmbH) | 5.0% | 5.0% | 5.0% |
| Diethylhexyl Carbonate (TEGOSOFT ® DEC, Evonik Operations GmbH) | 5.0% | 5.0% | 5.0% |
| *Persea Gratissima* (avocado) Oil | 2.0% | 2.0% | 2.0% |
| Polyglycery-3 Caprylate (TEGO ® Cosmo P813, Evonik Operations GmbH) | 0.5% | 0.5% | 0.5% |
| Zinc Ricinoleate (TEGODEO ® PY88 G, Evonik Operations GmbH) | 1.0% | 1.0% | 1.0% |
| Demineralized water | to 100% | to 100% | to 100% |
| Hydroxyethylcellulose (Natrosol 250 HHR (Ashland Specialty Chemicals) | 1.0% | 1.0% | 1.0% |
| Aluminum Chlorohydrate (50% aq.; Locron LIC, Clariant AG) | 15.0% | 15.0% | 15.0% |
| Methylisothiazolinone, Methylparaben, Ethylparaben; Dipropylene Glycol (Microcare MEM, Thor) | 0.8% | 0.8% | |
| Methylpropanediol; Caprylyl Glycol; Phenylpropanol (dermosoft ® OMP; Evonik Dr. Straetmans GmbH) | | | 3.5% |

Recipes 6a and 6b: Sun Care Spray SPF 30

| Recipe | 6a | 6b |
|---|---|---|
| Composition from example 4 | 4.0% | 4.0% |
| Phenoxyethyl Caprylate (TEGOSOFT ® XC, Evonik Operations GmbH) | 3.2% | 3.2% |
| Isopropyl Palmitate (TEGOSOFT ® P, Evonik Operations GmbH) | 2.0% | 2.0% |
| Bis-Ethylhexyloxyphenol Methoxyphenyl Triazine (Tinosorb S, BASF SE) | 3.0% | 3.0% |
| Butyl Methoxydibenzoylmethane | 2.0% | 2.0% |
| EHC | 2.0% | 2.0% |
| Ethylhexyl Salicylate | 4.0% | 4.0% |
| Octocrylene | 4.0% | 4.0% |
| Glycerin | 3.0% | 3.0% |
| Water | to 100% | to 100% |
| Carbomer suspension 1 (Acrylates/C10-30 Alkyl Acrylate Crosspolymer, TEGO ® Carbomer 341ER, Evonik Operations GmbH, 20% in Phenoxyethyl Caprylate) | 1.0% | 1.0% |
| Tris(hydroxymethyl)aminomethane (30% aq.) | 0.6% | 0.6% |
| UV filter solution (20% Phenylbenzimidazole Sulfonic Acid, 8.8% tris(hydroxymethyl)aminomethane, demineralized water to 100%) | 10.0% | 10.0% |
| Methylisothiazolinone, Methylparaben, Ethylparaben; Dipropylene Gly-col (Microcare MEM, Thor) | 0.8% | |
| Methylpropanediol; Caprylyl Glycol (dermosoft ® OM, Evonik Dr. Straetmans GmbH) | | 4.0 |

Recipes 7a and 7b: Sunscreen Spray

| Recipe | 7a | 7b | 7c |
|---|---|---|---|
| Composition from example 4 | 3.0% | 2.5% | 2.5% |
| Glyceryl Stearate Citrate (AXOL ® C 62, Evonik Operations GmbH) | | 0.5% | 0.5% |
| Glyceryl Stearate | 0.5% | 0.5% | 0.5% |
| Stearyl Alcohol | 0.5% | 0.5% | 0.5% |

-continued

| Recipe | 7a | 7b | 7c |
|---|---|---|---|
| Bis-Ethylhexyloxyphenol Methoxyphenyl Triazine (Tinosorb S, BASF SE) | 3.0% | 3.0% | 3.0% |
| Butyl Methoxydibenzoylmethane | 2.0% | 2.0% | 2.0% |
| Ethylhexyl Methoxycinnamate | 2.0% | 2.0% | 2.0% |
| Ethythexyl Salicylate | 4.0% | 4.0% | 4.0% |
| Octocrylene | 4.0% | 4.0% | 4.0% |
| Isopropyl Palmitate | 2.0% | 2.0% | 2.0% |
| Phenoxyethyl Caprylate (TEGOSOFT ® XC, Evonik Operations GmbH) | 3.2% | 3.2% | 3.2% |
| Glycerin | 3.0% | 3.0% | 3.0% |
| Demineralized water | to 100% | to 100% | to 100% |
| Carbomer suspension (Acrylates/C10-30 Alkyl Acrylate Crosspolymer, TEGO ® Carbomer 341ER, 20% in Phenoxyethyl Caprylate) | 1.0% | 1.0% | 1.0% |
| Tromethamine (30%) | 0.9% | 0.9% | 0.9% |
| UV filter solution (20% Phenylbenzimidazole Sulfonic Acid, 8.8% tris(hydroxymethyl)aminomethane, demineralized water to 100%) | 10.0% | 10.0% | 10.0% |
| Methylisothiazolinone, Methylparaben, Ethylparaben; Dipropylene Glycol (Microcare MEM, Thor) | 0.8% | 0.8% | |
| Methylpropanediol; Caprylyl Glycol; Phenylpropanol (dermosoft ® OMP; Evonik Dr. Straetmans GmbH) | | | 3.0% |

Recipes 8a, 8b and 8c: Sunscreen Lotion, SPF 30

| Recipe | 8a | 8b | 8c |
|---|---|---|---|
| Composition from example 4 | 3.00% | 2.00% | 2.00% |
| Cetearyl Glucoside (TEGO ® Care CG 90, Evonik Operations GmbH) | | 0.50% | 0.50% |
| Phenoxyethyl Caprylate (TEGOSOFT ® XC, Evonik Operations GmbH) | 8.00% | 8.00% | 8.00% |
| Diethylamino Hydroxybenzoyl Hexyl Benzoate (Uvinul A Plus, BASF SE) | 6.00% | 6.00% | 6.00% |
| Ethylhexyl Methoxycinnamate | 8.00% | 8.00% | 8.00% |
| Stearyl Alcohol | 1.00% | 1.00% | 1.00% |
| Glyceryl Stearate | 1.00% | 1.00% | 1.00% |
| Tocopheryl Acetate | 0.50% | 0.50% | 0.50% |
| Glycerin | 2.00% | 2.00% | 2.00% |
| Demineralized water | to 100% | to 100% | to 100% |
| Tromethamine | 0.90% | 0.90% | 0.90% |

-continued

| Recipe | 8a | 8b | 8c |
|---|---|---|---|
| Phenylbenzimidazole Sulfonic Acid | 2.00% | 2.00% | 2.00% |
| Acrylates/C10-30 Alkyl Acrylate Crosspolymer (TEGO ® Carbomer 341 ER, Evonik Operations GmbH) | 0.30% | 0.30% | 0.30% |
| Sodium hydroxide (10% aq.) | q.s. | q.s. | q.s. |
| Methylisothiazolinone, Methylparaben, Ethylparaben; Dipropylene Glycol (Microcare MEM, Thor) | 0.80% | 0.80% | |
| Caprylyl Glycol; Glycerin; Glyceryl Caprylate; Phenylpropanol; Aqua (dermosoft ® LP MB; Evonik Dr. Straetmans GmbH) | | | 1.0 |

Recipes 9a, 9b and 9c. Sunscreen Lotion SPF 30, High UVA Protection

| Recipe | 9a | 9b | 9c |
|---|---|---|---|
| Composition from example 4 | 3.00% | 2.50% | 2.50% |
| Sodium Cetearyl Sulfate (Lanette E, BASF SE) | | 0.50% | 0.50% |
| Phenoxyethyl Caprylate (TEGOSOFT ® XC, Evonik Operations GmbH) | 7.30% | 7.30% | 7.30% |
| Butyl Methoxydibenzoylmethane | 5.00% | 5.00% | 5.00% |
| Diethylhexyl Butamido Triazone (UVAsorb HEB, 3V Sigma) | 1.00% | 1.00% | 1.00% |
| Ethylhexyl Salicylate | 1.50% | 1.50% | 1.50% |
| Octocrylene | 3.50% | 3.50% | 3.50% |
| Titanium Dioxide; Diethylhexyl Carbonate; Polyglyceryl-6 Polyhydroxystearate (TEGO ® Sun TDEC 45, Evonik Operations GmbH) | 2.20% | 2.20% | 2.20% |
| Stearyl Alcohol | 1.00% | 1.00% | 1.00% |
| Nylon-10/10 (TEGOLON ® ECO 10-10, Evonik Operations GmbH) | 0.50% | 0.50% | 0.50% |
| Glyceryl Stearate | 1.00% | 1.00% | 1.00% |
| Tocopheryl Acetate | 0.50% | 0.50% | 0.50% |
| Glycerin | 2.00% | 2.00% | 2.00% |
| Demineralized water | to 100% | to 100% | to 100% |
| Citric Acid (50% aq.) | 0.10% | 0.10% | 0.10% |
| Bis-Ethylhexyloxyphenol Methoxyphenyl Triazine (Tinosorb S, BASF SE) | 20.00% | 20.00% | 20.00% |
| Acrylates/C 10-30 Alkyl Acrylate Crosspolymer (TEGO ® Carbomer 341 ER, Evonik Operations GmbH) | 0.30% | 0.30% | 0.30% |

-continued

| Recipe | 9a | 9b | 9c |
|---|---|---|---|
| Sodium Hydroxide (10% aq.) | 0.90% | 0.90% | 0.90% |
| Methylisothiazolinone, Methylparaben, Ethylparaben; Dipropylene Glycol (Microcare MEM, Thor) | 0.80% | 0.80% | |
| Triethyl Citrate; Caprylyl Glycol; Benzoic Acid (Verstatil ® TBO; Evonik Dr. Straetmans GmbH) | | | 1.0% |

Recipes 10a, 10b and 10c: Sunscreen Lotion, SPF 30

| Recipe | 10a | 10b | 10c |
|---|---|---|---|
| Composition from example 4 | 3.00% | 2.00% | 2.00% |
| Methyl Glucose Sesquistearate (TEGO ® Care PS, Evonik Operations GmbH) | | 1.00% | 1.00% |
| Phenoxyethyl Caprylate (TEGOSOFT ® XC, Evonik Operations GmbH) | 1.50% | 1.50% | 1.50% |
| Octocrylene | 10.00% | 10.00% | 10.00% |
| Butyl Methoxydibenzoylmethane | 3.50% | 3.50% | 3.50% |
| Titanium Dioxide; Diethylhexyl Carbonate; Polyglyceryl-6 Polyhydroxystearate (TEGO ® Sun TDEC 45, Evonik Operations GmbH) | 14.50% | 14.50% | 14.50% |
| Stearyl Alcohol | 0.20% | 0.20% | 0.20% |
| Glyceryl Stearate | 0.20% | 0.20% | 0.20% |
| Tocopheryl Acetate | 0.50% | 0.50% | 0.50% |
| Glycerin | 2.00% | 2.00% | 2.00% |
| Demineralized water | to 100% | to 100% | to 100% |
| Acrylates/C10-30 Alkyl Acrylate Crosspolymer (TEGO ® Carbomer 341 ER, Evonik Operations GmbH) | 0.20% | 0.20% | 0.20% |
| Sodium Hydroxide (10% aq.) | 0.60% | 0.60% | 0.60% |
| Methylisothiazolinone, Methylparaben, Ethylparaben; Dipropylene Glycol (Microcare MEM, Thor) | 0.80% | 0.80% | |
| Methylpropanediol; Caprylyl Glycol; Phenylpropanol (dermosoft ® OMP; Evonik Dr. Straetmans GmbH) | | | 3.0% |

Recipes 11a, 11b and 11c: Sunscreen Lotion SPF 50, High UVA Protection

| Recipe | 11a | 11b | 11c |
|---|---|---|---|
| Composition from example 4 | 3.00% | 2.50% | 2.50% |
| Polyglycery-3 Methylglucose Distearate (TEGO ® Care 450, Evonik Operations GmbH) | | 0.50% | 0.50% |
| Phenoxyethyl Caprylate (TEGOSOFT ® XC, Evonik Operations GmbH) | 2.00% | 2.00% | 2.00% |
| Nylon-10/10 (TEGOLON ® ECO 10-10, Evonik Operations GmbH) | 0.50% | 0.50% | 0.50% |
| Butyl Methoxydibenzoylmethane | 5.00% | 5.00% | 5.00% |
| Diethylhexyl Butamido Triazone (UVAsorb HEB, 3V Sigma) | 1.00% | 1.00% | 1.00% |
| Bis-Ethylhexyloxyphenol Methoxyphenyl Triazine (Tinosorb S, BASF SE) | 3.00% | 3.00% | 3.00% |
| Ethylhexyl Salicylate | 1.00% | 1.00% | 1.00% |
| Octocrylene | 8.00% | 8.00% | 8.00% |
| Stearyl Alcohol | 0.45% | 0.45% | 0.45% |
| Glyceryl Stearate | 0.45% | 0.45% | 0.45% |
| Xanthan Gum (Keltrol CG-SFT, CP Kelco) | 0.30% | 0.30% | 0.30% |
| Tocopheryl Acetate | 0.50% | 0.50% | 0.50% |
| Hydroxyethylcellulose (Natrosol 250 HHR (Ashland Specialty Chemicals) | 0.50% | 0.50% | 0.50% |
| Demineralized water | to 100% | to 100% | to 100% |
| Sodium Hydroxide (10% aq., pH adjustment to 7.5) | q.s. | q.s. | q.s. |
| Disodium Phenyl Dibenzimidazole Tetrasulfonate (Neoheliopan AP, Symrise) | 5.00% | 5.00% | 5.00% |
| Methylene Bis-Benzotriazolyl Tetramethylbutylphenol (Tinosorb M, BASF SE) | 8.00% | 8.00% | 8.00% |
| Methylisothiazolinone, Methylparaben, Ethylparaben; Dipropylene Glycol (Microcare MEM, Thor) | 0.80% | 0.80% | |
| Methylpropanediol; Caprylyl Glycol (dermosoft ® OM, Evonik Dr. Straetmans GmbH) | | | 3.8% |

Recipes 12a, 12b and 12c: Sunscreen Lotion, SPF 50

| Recipe | 12a | 12b | 12c |
|---|---|---|---|
| Composition from example 4 | 3.50% | 3.00% | 3.00% |
| Glyceryl Stearate Citrate (AXOL ® C 62, Evonik Operations GmbH) | | 1.00% | 1.00% |
| Phenoxyethyl Caprylate (TEGOSOFT ® XC, Evonik Operations GmbH) | 2.50% | 2.50% | 2.50% |
| Diethylamino Hydroxybenzoyl Hexyl Benzoate | 10.00% | 10.00% | 10.00% |
| Ethylhexyl Methoxycinnamate | 10.00% | 10.00% | 10.00% |
| Stearyl Alcohol | 1.00% | 1.00% | 1.00% |
| Glyceryl Stearate | 1.00% | 1.00% | 1.00% |
| Xanthan Gum (Keitrol CG-SFT, CP Kelco) | 0.50% | 0.50% | 0.50% |
| Tocopheryl Acetate | 0.50% | 0.50% | 0.50% |
| Glycerin | 2.00% | 2.00% | 2.00% |
| Demineralized water | to 100% | to 100% | to 100% |
| Phenylbenzimidazole Sulfonic Acid | 4.00% | 4.00% | 4.00% |
| Tromethamine | 1.80% | 1.80% | 1.80% |
| Methylisothiazolinone, Methylparaben, Ethylparaben; Dipropylene Glycol (Microcare MEM, Thor) | 0.80% | 0.80% | |
| Triethyl Citrate; Glyceryl Caprylate; Benzoic Acid (Verstatil ® TBG MB, Evonik Dr. Straetmans GmbH) | | | 1.2% |

Recipes 13a, 13b and 13c: Sunscreen Lotion SPF 50+

| Recipe | 13a | 13b | 13c |
|---|---|---|---|
| Composition from example 4 | 3.00% | 2.5% | 2.5% |
| Potassium Cetyl Phosphate | | 1.0% | 1.0% |
| Phenoxyethyl Caprylate (TEGOSOFT ® XC, Evonik Operations GmbH) | 3.00% | 3.00% | 3.00% |
| Butyl Methoxydibenzoylmethane | 5.00% | 5.00% | 5.00% |
| Octocrylene | 4.90% | 4.90% | 4.90% |
| Ethylhexyl Methoxycinnamate | 0.10% | 0.10% | 0.10% |
| Bis-Ethylhexyloxyphenol Methoxyphenyl Triazine (Tinosorb S, BASF SE) | 4.70% | 4.70% | 4.70% |
| Diethylhexyl Butamido Triazone (UVAsorb HEB, 3V Sigma) | 3.70% | 3.70% | 3.70% |
| Titanium Dioxide; Diethylhexyl Carbonate; Polyglyceryl-6 Polyhydroxystearate (TEGO ® Sun TDEC 45, Evonik Operations GmbH) | 11.00% | 11.00% | 11.00% |
| Stearyl Alcohol | 0.50% | 0.50% | 0 50% |
| Glyceryl Stearate | 0.50% | 0.50% | 0.50% |
| Xanthan Gum (Keltrol CG-SFT, CP Kelco) | 0.20% | 0.20% | 0.20% |
| Glycerin | 2.00% | 2.00% | 2.00% |
| Demineralized water | to 100% | to 100% | to 100% |
| Methylisothiazolinone, Methylparaben, Ethylparaben; Dipropylene Glycol (Microcare MEM, Thor) | 0.80% | 0.80% | |
| Triethyl Citrate; Caprylyl Glycol; Benzoic Acid (Verstatil ® TBO; Evonik Dr. Straetmans GmbH) | | | 0.9% |

Recipes 14a and 14b: Body Lotion

| Recipe | 14a | 14b |
|---|---|---|
| Composition from example 4 | 4.0% | 4.0% |
| Isoamyl Cocoate (TEGOSOFT ® AC, Evonik Operations GmbH) | 2.5% | 2.5% |
| Caprylic/Capric Triglyceride (TEGOSOFT ® CT, Evonik Operations GmbH) | 3.5% | 3.5% |
| Water | to 100% | to 100% |
| Creatine (TEGO ® Cosmo C 100, Evonik Operations GmbH) | 0.5% | 0.5% |
| Carbomer suspension 2 (Carbomer, TEGO ® Carbomer 141, Evonik Operations GmbH, 20% in Ethylhexyl Stearate) | 1.0% | 1.0% |
| Sodium Hydroxide (10% aq.) | 0.6% | 0.6% |
| Phenoxyethanol, Ethylhexylglycerin (Euxyl PE 9010, Schülke & Mayr GmbH) | 0.7% | |
| Aqua; Sodium Levulinate; Sodium Benzoate (Verstatil ® BL; Evonik Dr. Straetmans GmbH) | | 1.5% |
| Glyceryl Caprylate (dermosoft ® GMCY MB; Evonik Dr. Straetmans GmbH) | | 0.3% |

Recipes 15a and 15b: Natural Care Cream

| Recipe | 15a | 15b |
|---|---|---|
| Composition from example 4 | 6.0% | 6.0% |
| Caprylic/Capric Triglyceride (TEGOSOFT ® CT, Evonik Operations GmbH) | 8.0% | 8.0% |
| Isopropyl Palmitate (TEGOSOFT ® P, Evonik Operations GmbH) | 11.0% | 11.0% |
| Prunus Amygdalus Duicis (sweet almond) Oil | 10.0% | 10.0% |
| Water | to 100% | to 100% |
| Glycerin | 3.0% | 3.0% |
| Sodium Hydroxide (10% aq.) | 0.2% | 0.2% |
| Benzyl Alcohol, Benzoic Acid, Sorbic Acid (Rokonsal BSB-N, Ashland Specialty Ingredients) | 0.8% | |
| Glycerin; Aqua; Sodium Levulinate; Sodium Anisate (dermosoft ® 1388 eco; Evonik Dr. Straetmans GmbH) | | 3% |
| Glyceryl Caprylate (dermosoft ® GMCY MB; Evonik Dr. Straetmans GmbH) | | 0.2% |

Recipe 16a and 16b: Anti-Ageing Cream

| Recipe | 16a | 16b |
|---|---|---|
| Composition from example 4 | 6.0% | 6.0% |
| Caprylic/Capric Triglyceride (TEGOSOFT ® CT, Evonik Operations GmbH) | 9.5% | 9.5%l |
| C12-15 Alkyl Benzoate (TEGOSOFT ® TN, Evonik Operations GmbH) | 9.5% | 9.5% |
| Water | to 100% | to 100% |
| Glycerin | 3.0% | 3.0% |
| Tetrapeptide-21; Glycerin; Butylene Glycol; Aqua (TEGO ® Pep 4-17, Evonik Operations) | 4.0% | 4.0% |
| Sodium Hyaluronate (HyaCare ®, Evonik Operations GmbH) | 0.1% | 0.1% |
| Hydrolyzed Hyaluronic Acid (HyaCare ® 50, Evonik Operations GmbH) | 0.1% | 0.1% |
| Aqua; Ethylhexyl Stearate; Sodium Hyaluronate Crosspolymer; Polyglyceryl-4 Diisostearate/Polyhydroxystearate/Sebacate; Sodium Isostearate (HyaCare ® Filler CL, Evonik Operations GmbH) | 5.0% | 5.0% |
| Methylisothiazolinone, Methylparaben, Ethylparaben; Dipropylene Glycol (Microcare MEM, Thor) | 0.8% | |
| Aqua; Sodium Levulinate; Potassium Sorbate (VERSTATIL SL non GMO; Evonik Dr. Straetmans GmbH9 | | 1.2% |
| Caprylyl Glycol (dermosoft ® Octiol; Evonik Dr. Straetmans GmbH) | | 0.2% |

Recipe 17a and 17b: O/W Foundation

| Recipe | 17a | 17b |
|---|---|---|
| Composition from example 4 | 6.0% | 6.0% |
| Myristyl Myristate (TEGOSOFT ® MM, Evonik Operations GmbH) | 2.0% | 2.0% |
| Isopropyl Myristate (TEGOSOFT ® M, Evonik Operations GmbH) | 6.0% | 6.0% |
| Decyl Cocoate (TEGOSOFT ® DC, Evonik Operations GmbH) | 6.0% | 6.0% |
| Cetyl Ricinoleate (TEGOSOFT ® CR, Evonik Operations GmbH) | 1.0% | 1.0% |
| Water | to 100% | to 100% |
| Glycerin | 1.0% | 1.0% |
| Titanium Dioxide (Hombitan AC 360, Sachtleben) | 8.0% | 8.0% |
| Iron Oxides (Sicovit Yellow 72, Rockwood Pigments) | 0.9% | 0.9% |
| Iron Oxides (Sicovit Red E 172, Rockwood Pigments) | 0.2% | 0.2% |
| Iron Oxides (Sicovit Brown 172, Rockwood Pigments) | 0.4% | 0.4% |
| Iron Oxides (Sicovit Black 80 E 172, Rockwood Pigments) | 0.1% | 0.1% |
| Cellulose (TEGO ® Feel Green, Evonik Operations GmbH) | 2.0% | 2.0% |
| Sodium Hydroxide (10% aq.) | 0.2% | 0.2% |
| Benzyl Alcohol, Benzoic Acid, Sorbic Acid (Rokonsal BSB-N, Ashland Specialty Ingredients) | 1.0% | |
| Methylpropanediol; Caprylyl Glycol; Phenylpropanol (dermosoft ® OMP; Evonik Dr. Straetmans GmbH) | | 3.2% |

Recipes 18a, 18b, 18c and 18d: Lotions with Cosmetic Active Ingredients

| Recipe | 18a | 18b | 18c | 18d |
|---|---|---|---|---|
| Composition from example 4 | 3.5% | 3.5% | 3.0% | 3.0% |
| Stearic Acid | | | 0.5% | 0.5% |
| Glyceryl Stearate | 0.5% | 0.6% | 0.6% | 0.6% |
| Cetearyl Alcohol | 0.5% | 0.6% | 0.6% | 0.6% |
| Caprylic/Capric Triglyceride | 8.5% | 8.5% | 8.5% | 8.5% |
| Ethylhexyl Palmitate (TEGOSOFT ® OP, Evonik Operations GmbH) | 8.5% | 8.5% | 8.5% | 8.5% |
| Demineralized water | to 100% | to 100% | to 100% | to 100% |
| Xanthan Gum (Keltrol CG-SFT, CP Kelco) | 0.8% | 0.8% | 0.8% | 0.8% |
| Terminalia Arjuna Bark Extract; Pentylene Glycol (proposed; TEGO ® Arjuna S, Evonik Operations GmbH) | | 2.0% | 2.0% | 2.0% |
| Betaine; Urea; Potassium Lactate; Sodium Polyglutamate (proposed); Hydrolyzed Sclerotium Gum (TEGO ® Smooth; Evonik Operations GmbH) | 5.0% | | | |
| Phenoxyethanol, Methylparaben, Ethylparaben, Propylparaben (Phenonip XB (Clariant International Ltd.) | 1.0% | | | |

-continued

| Recipe | 18a | 18b | 18c | 18d |
|---|---|---|---|---|
| Methylisothiazolinone, Methylparaben, Ethylparaben; Dipropylene Glycol (Microcare MEM, Thor) | | 0.8% | 0.8% | |
| Caprylyl Glycol; Glyceryl Caprylate; Dipropylene Glycol (dermosoft ® MCAV MB; Evonik Dr. Straetmans GmbH) | | | | 1.0% |

Recipes 19a, 19b and 19c: Lotion with Low Oil Phase Content

| Recipe | 19a | 19b | 19c |
|---|---|---|---|
| Composition from example 4 | 3.0% | 2.0% | 2.0% |
| Polyglyceryl-3 Dicitrate/Stearate (TEGO ® Care PSC 3 (Evonik Operations GmbH) | | 1.0% | 1.0% |
| Cetearyl Alcohol | 0.5% | 0.5% | 0.5% |
| Caprylic/Capric Triglyceride | 6.5% | 6.5% | 6.5% |
| Demineralized water | to 100% | to 100% | to 100% |
| Xanthan Gum (Keltrol CG-SFT, CP Kelco) | 0.5% | 0.5% | 0.5% |
| Methylisothiazolinone, Methylparaben, Ethylparaben; Dipropylene Glycol (Microcare MEM, Thor) | 0.8% | 0.8% | |
| Glycerin; Aqua; Sodium Levulinate; Sodium Anisate (dermosoft ® 1388; Evonik Dr. Straetmans GmbH | | | 3.0% |

Recipes 20a, 20b 20c and 20d: O/W Serums 1

| Recipe | 20a | 20b | 20c | 20d |
|---|---|---|---|---|
| Composition from example 4 | 2.5% | 2.5% | 4.0% | 4.0% |
| Sodium Stearoyl Glutamate (Eumulgin SG, BASF SE) | | 1.0% | | |
| Glyceryl Stearate | | | 0.75% | 0.75% |
| Stearyl Alcohol | | | 0.75% | 0.75% |
| Caprylic/Capric Triglyceride | 2.0% | 2.0% | 2.0% | 2.0% |
| Oleyl Erucate (TEGOSOFT ® OER, Evonik Operations GmbH) | 2.0% | 2.0% | 2.0% | 2.0% |
| Isoamyl Cocoate (TEGOSOFT ® AC, Evonik Operations GmbH) | | | 3.0% | 3.0% |
| Persea Gratissima (avocado) Oil | 1.0% | 1.0% | 1.0% | 1.0% |
| Aqua; Ethylhexyl Stearate; Sodium Hyaluronate Crosspolymer; Polyglyceryl-4 DiIsostearate/Polyhydroxystearate/Sebacate; Sodium Isostearate (HyaCare ® Filler CL, Evonik Operations) | 3.0% | 3.0% | | |
| Demineralized water | to 100% | to 100% | to 100% | to 100% |
| Butylene Glycol | 5.0% | 5.0% | 5.0% | 5.0% |
| Tetrapeptide-21; Glycerin; Butylene Glycol; Aqua (TEGO ® Pep 4-17, Evonik Operations) | 2.0% | 2.0% | 2.0% | 2.0% |
| Hydrolyzed Hyaluronic Acid (HyaCare ® 50, Evonik Operations) | 0.1% | 0.1% | 0.1% | 0.1% |
| Xanthan Gum (Keltrol CG-SFT, CP Kelco) | 0.5% | 0.5% | 0.5% | 0.5% |
| Sodium Hydroxide (10% aq.) | 0.2% | 0.2% | 0.2% | 0.2% |
| Benzyl Alcohol, Benzoic Acid, Sorbic Acid (Rokonsal BSB-N, Ashland Specialty Ingredients) | 0.8% | 0.8% | 0.8% | |
| Polygiutamic Acid; Sclerotium glucan; Betaine; Urea; Potassium Lactate (TEGO ® Smooth Complex, Evonik Operations) | 3.0% | 3.0% | 3.0% | 3.0% |
| Triethyl Citrate; Glyceryl Caprylate; Benzoic Acid (Verstatil ® TBG; Evonik Dr. Straetmans GmbH) | | | | 1.2% |

Recipes 20e, 20f, 20g and 20h: O/W Serums 2

| Recipe | 20e | 20f | 28g | 20h |
|---|---|---|---|---|
| Composition from example 4 | 3.0% | 3.0% | 2.0% | 2.0% |
| Cetearyl Glucoside (TEGO ® Care CG 90, Evonik Operations GmbH) | 0.5% | | | |
| Polyglyceryl-3 Dicitrate/Stearate (TEGO ® Care PSC 3, Evonik Operations GmbH) | | | 1.5% | 1.5% |
| Glyceryl Stearate | 0.75% | 0.5% | 0.5% | 0.5% |
| Stearyl Alcohol | 0.75% | 0.5% | 0.5% | 0.5% |
| Caprylic/Capric Triglyceride | 2.0% | 2.0% | 2.0% | 2.0% |
| Oleyl Erucate (TEGOSOFT ® OER, Evonik Operations GmbH) | 2.0% | 2.0% | 2.0% | 2.0% |
| Isoamyl Cocoate (TEGOSOFT ® AC, Evonik Operations GmbH) | 3.0% | | | |
| Persea Gratissima (avocado) Oil | 1.0% | 1.0% | 1.0% | 1.0% |
| Aqua; Ethylhexyl Stearate; Sodium Hyaluronate Crosspolymer; Polyglyceryl-4 Diisostearate/Polyhydroxystearate/Sebacate; Sodium Isostearate (HyaCare ® Filler CL, Evonik Operations) | | 3.0% | 3.0% | 3.0% |
| Demineralized water | to 100% | to 100% | to 100% | to 100% |
| Butylene Glycol | 5.0% | 5.0% | 5.0% | 5.0% |
| Tetrapeptide-21; Glycerin; Butylene Glycol; Aqua (TEGO ® Pep 4-17, Evonik Operations) | 2.0% | 2.0% | 2.0% | 2.0% |
| Hydrolyzed Hyaluronic Acid (HyaCare ® 50, Evonik Operations) | 0.1% | 0.1% | 0.1% | 0.1% |
| Xanthan Gum (Keltrol CG-SFT, CP Kelco) | 0.5% | 0.5% | 0.5% | 0.5% |
| Sodium Hydroxide (10% aq.) | 0.2% | 0.2% | 0.2% | 0.2% |
| Benzyl Alcohol, Benzoic Acid, Sorbic Acid (Rokonsal BSB-N, Ashland Specialty Ingredients) | 0.8% | 0.8% | 0.8% | |
| Polyglutamic Acid; Sclerotium glucan; Betaine; Urea; Potassium Lactate (TEGO ® Smooth Complex, Evonik Operations) | 3.0% | | | 3.0% |
| Triethyl Citrate; Caprylyl Glycol; Benzoic Acid (Verstatil ® TBO; Evonik Dr. Straetmans GmbH) | | | | 1.0% |

Recipes 21a, 21b and 21c: O/W Blemish Balm Lotion

| Recipe | 21a | 21b | 21c |
|---|---|---|---|
| Composition from example 4 | 4.00% | 3.00% | 3.00% |
| Polyglycery-3 Methylglucose Distearate (TEGO ® Care 450, Evonik Operations GmbH) | | 1.00% | 1.00% |
| Glyceryl Stearate | 0.75% | 0.75% | 0.75% |
| Stearyl Alcohol | 0.75% | 0.75% | 0.75% |
| Diethylhexyl Carbonate (TEGOSOFT ® DEC, Evonik Operations GmbH) | 7.40% | 7.40% | 7.40% |
| Aqua; Ethylhexyl Stearate; Sodium Hyaluronate Crosspolymer; Polyglyceryl-4 Diisostearate/Polyhydroxystearate/Sebacate; Sodium Isostearate (HyaCare ® Filler CL, Evonik Operations) | 2.00% | 2.00% | 2.00% |
| Ethylhexyl Methoxycinnamate | 5.00% | 5.00% | 5.00% |
| Diethylamino Hydroxybenzoyl Hexyl Benzoate (Uvinul A Plus, BASF SE) | 3.00% | 3.00% | 3.00% |
| Phytosphingosine | 0.10% | 0.10% | 0.10% |
| Hydrolyzed Hyaluronic Acid (HyaCare ® 50, Evonik Operations) | 0.10% | 0.10% | 0.10% |
| Tetrapeptide-21; Glycerin; Butylene Glycol; Aqua (TEGO ® Pep 4-17, Evonik Operations) | 2.00% | 2.00% | 2.00% |
| Demineralized water | to 100% | to 100% | to 100% |
| Titanium Dioxide (Hombitan AC 360, Sachtleben) | 3.00% | 3.00% | 3.00% |
| Talc | 2.00% | 2.00% | 2.00% |
| Iron Oxide (Unipure Yellow LC 182, Sensient Technologies) | 0.36% | 0.36% | 0.36% |
| Iron Oxide (Unipure Red LC 381, Sensient Technologies) | 0.12% | 0.12% | 0.12% |
| Iron Oxide (Unipure Black LC 989, Sensient Technologies) | 0.08% | 0.08% | 0.08% |
| Isoamyl Cocoate (TEGOSOFT ® AC, Evonik Operations GmbH) | 4.44% | 4.44% | 4.44% |
| Phenoxyethyl Caprylate (TEGOSOFT ® XC, Evonik Operations GmbH) | 4.00% | 4.00% | 4.00% |
| Nylon-10/10 (TEGOLON ® ECO 10-10, Evonik Operations GmbH) | 3.00% | 3.00% | 3.00% |
| Glycerin | 3.00% | 3.00% | 3.00% |
| Xanthan Gum (Keltrol CG-SFT, CP Kelco) | 0.50% | 0.50% | 0.50% |
| Ethanol | 3.00% | 3.00% | 3.00% |
| Methylisothiazolinone, Methylparaben, Ethylparaben; Dipropylene Glycol (Microcare MEM, Thor) | 0.80% | 0.80% | |
| Methylpropanediol; Caprylyl Glycol (dermosoft ® OM, Evonik Dr. Straetmans GmbH) | | | 4.0% |

Recipes 22a, 22b, 22c and 22d: Lotion for Sensitive Skin

| Recipe | 22a | 22b | 22c | 22d |
|---|---|---|---|---|
| Composition from example 4 | 3.0% | 3.0% | 3.0% | 3.0% |
| Glyceryl Stearate | 0.5% | 1.0% | 0.5% | 0.5% |
| Cetearyl Alcohol | 1.0% | 1.0% | 1.0% | 1.0% |
| Butyrospermum Parkii Butter (shea butter) | 3.0% | 3.0% | 3.0% | 3.0% |
| Caprylic/Capric Triglyceride | 5.0% | 5.0% | 5.0% | 5.0% |
| Isopropyl Palmitate (TEGOSOFT ® P, Evonik Operations GmbH) | 5.0% | 5.0% | 5.0% | 5.0% |
| Xanthan Gum (Keltrol CG-SFT, CP Kelco) | 0.2% | 0.2% | 0.2% | 0.2% |
| Glycerin | 5.0% | 5.0% | 5.0% | 5.0% |
| Urea | 10.0% | 15.0% | 20.0% | 20.0% |
| Demineralized water | to 100% | to 100% | to 100% | to 100% |
| Phenoxyethanol, Ethylhexylglycerin (Euxyl PE 9010, Schülke & Mayr GmbH) | 0.7% | | | |
| Sodium Hydroxide (10% aq.) (pH adjustment to 5.0) | | q.s. | | |
| Sodium Benzoate, Potassium Sorbate (Euxyl K 712, Schülke & Mayr GmbH) | | 1.2% | | |
| Methylisothiazolinone, Methylparaben, Ethylparaben; Dipropylene Glycol (Microcare MEM, Thor) | | | 0.8% | |
| Sodium Anisate (dermosoft ® anisate; Evonik Dr. Straetmans GmbH) | | | | 0.12% |
| Levulinic Acid; Sodium Levulinate; Glycerin; Aqua (dermosoft ® 700B; Evonik Dr. Straetmans GmbH) | | | | 1.0% |
| Glyceryl Caprylate (dermosoft ® GMC MB; Evonik Dr. Straetmans GmbH) | | | | 0.3% |

Recipes 23a, 23b, 23c and 23d: Care Lotion for Dry Skin 1

| Recipe | 23a | 23b | 23c | 23d |
|---|---|---|---|---|
| Composition from example 4 | 3.0% | 2.5% | 3.0% | 3.0% |
| Sodium Stearoyl Glutamate (Eumulgin SG, BASF SE) | | 1.0% | | |
| Glyceryl Stearate | 1.0% | 1.0% | 1.5% | 1.5% |
| Cetearyl Alcohol | 1.0% | 1.0% | 1.5% | 1.5% |
| Cetyl Ricinoleate | 2.0% | 2.0% | 2.0% | 2.0% |
| Oleyl Erucate (TEGOSOFT ® OER, Evonik Operations GmbH) | 5.0% | 5.0% | 5.0% | 5.0% |
| Isoamyl Cocoate (TEGOSOFT ® AC, Evonik Operations GmbH) | 8.0% | 8.0% | 8.0% | 8.0% |
| Decyl Cocoate (TEGOSOFT ® DC, Evonik Operations GmbH) | 3.0% | 3.0% | 3.0% | 3.0% |
| Xanthan Gum (Keltrol CG-SFT, CP Kelco) | 0.2% | 0.2% | 0.2% | 0.2% |
| Glycerin | 5.0% | 5.0% | 5.0% | 5.0% |
| Urea | 10.0% | 10.0% | 15.0% | 15.0% |
| Demineralized water | to 100% | to 100% | to 100% | to 100% |
| Methylisothiazolinone, Methylparaben, Ethylparaben; Dipropylene Glycol (Microcare MEM, Thor) | 0.8% | 0.8% | 0.8% | |
| Phenethyl Alcohol (dermosoft ® PEA; Evonik Dr. Straetmans GmbH) | | | | 1.0% |

Recipes 23e, 23f, 23g and 23h: Care Lotion for Dry Skin 2

| Recipe | 23e | 23f | 23g | 23h |
|---|---|---|---|---|
| Composition from example 4 | 2.5% | 3.0% | 3.0% | 3.0% |
| Polyglyceryl-6 Distearate | 0.5% | | | |
| Stearic Acid | | | 0.5% | 0.5% |
| Glyceryl Stearate | 1.5% | 1.5% | 1.5% | 1.5% |
| Cetearyl Alcohol | 1.5% | 1.5% | 1.5% | 1.5% |
| Cetyl Ricinoleate | 2.0% | 2.0% | 2.0% | 2.0% |
| Oleyl Erucate (TEGOSOFT ® OER, Evonik Operations GmbH) | 5.0% | 5.0% | 5.0% | 5.0% |
| Isoamyl Cocoate (TEGOSOFT ® AC, Evonik Operations GmbH) | 8.0% | 8.0% | 8.0% | 8.0% |
| Decyl Cocoate (TEGOSOFT ® DC, Evonik Operations GmbH) | 3.0% | 3.0% | 3.0% | 3.0% |
| Xanthan Gum (Keltrol CG-SFT, CP Kelco) | 0.2% | 0.2% | 0.2% | 0.2% |
| Glycerin | 5.0% | 5.0% | 5.0% | 5.0% |

-continued

| Recipe | 23e | 23f | 23g | 23h |
|---|---|---|---|---|
| Urea | 15.0% | 20.0% | 20.0% | 20.0% |
| Demineralized water | to 100% | to 100% | to 100% | to 100% |
| Methylisothiazolinone, Methylparaben, Ethylparaben; Dipropylene Glycol (Microcare MEM, Thor) | 0.8% | 0.8% | 0.8% | |
| Phenylpropanol (dermosoft ® 250 eco; Evonik Dr. Straetmans GmbH) | | | | 0.4% |
| 1,2-Hexanediol (dermosoft ® Hexiol; Evonik Dr. Straetmans GmbH) | | | | 3.0% |

Recipes 24a, 24b and 24c: Preservative-Free Lotions 1

| Recipe | 24a | 24b | 24c |
|---|---|---|---|
| Composition from example 4 | 3.0% | 2.0% | 3.0% |
| (AXOL ® C 62, Evonik Operations GmbH) | | 1.0% | |
| Glyceryl Stearate | 0.2% | 0.2% | 0.5% |
| Stearyl Alcohol | 0.2% | 0.2% | 0.5% |
| Prunes Amygdalus Dulcis (sweet almond) Oil | 10.0% | 10.0% | 10.0% |
| Isoamyl Cocoate (TEGOSOFT ® AC, Evonik Operations GmbH) | 6.6% | 6.6% | 6.0% |
| Glycerin | 4.0% | 4.0% | 4.0% |
| Demineralized water | to 100.0% | to 100.0% | to 100.0% |
| Caprylyl Glycol, Glycerin, Glyceryl Caprylate, Phenylpropanol (Dermosoft ® LP, Evonik Dr. Straetmans GmbH) | 1.0% | 1.0% | |
| Methylpropanediol, Caprylyl Glycol, Phenylpropanol (Dermosoft ® OMP, Evonik Dr. Straetmans GmbH) | | | 4.0% |
| Xanthan Gum (Keltrol CG-SFT, CP Kelco) | 0.5% | 0.5% | 0.5% |

Recipes 24d, 24e and 24f: Preservative-Free Lotions 2

| Recipe | 24d | 24e | 24f |
|---|---|---|---|
| Composition from example 4 | 3.0% | 3.0% | 1.5% |
| Glyceryl Stearate SE | 0.5% | | |
| Polyglyceryl-3 Dicitrate/Stearate (TEGO ® Care PSC 3, Evonik Operations GmbH) | | | 1.5% |
| Glyceryl Stearate | 0.5% | 0.5% | 0.5% |
| Stearyl Alcohol | 0.5% | 0.5% | 0.5% |
| Prunus Amygdalus Dulcis (sweet almond) Oil | 10.0% | 10.0% | 10.0% |
| Isoamyl Cocoate (TEGOSOFT ® AC, Evonik Operations GmbH) | 6.0% | 6.0% | 6.0% |
| Glycerin | 4.0% | 4.0% | 4.0% |
| Demineralized water | to 100.0% | to 100.0% | to 100.0% |
| Methylpropanediol, Caprylyl Glycol, Phenylpropanol (Dermosoft ® OMP, Evonik Dr. Straetmans GmbH) | 4.0% | | |
| Caprylyl Glycol (Dermosoft ® Octiol, Evonik Dr. Straetmans GmbH) | | 0.4% | 0.4% |
| p-Anisic Acid 10% solution (dissolve 3.0 g of Sodium Hydroxide in 56.5 g of demineralized water, add 30.0 g of Glycerin and 10.0 g of Dermosoft ® Octiol [Evonik Dr. Straetmans GmbH], and stir until the solution is clear) | | 2.0% | 2.0% |
| Citric Acid (10% aq.) (pH adjustment to 6.0) | | q.s. | q.s. |
| Xanthan Gum (Keltrol CG-SFT, CP Kelco) | 0.5% | 0.5% | 0.5% |

Recipes 25a and 25b: W/O Lotion

| Recipe | 25a | 25b |
|---|---|---|
| Composition from example 5 | 2.0% | 2.0% |
| Beeswax | 0.5% | 0.5% |
| Castor wax | 0.5% | 0.5% |
| Paraffinum perliquidum | 10.5% | 10.5% |
| Decyl Cocoate (TEGOSOFT ® DC, Evonik Operations GmbH) | 8.0% | 8.0% |
| Tocopheryl Acetate | 0.5% | 0.5% |
| Cyclopentasiloxane | 6.0% | 6.0% |
| Sodium Chloride | 0.5% | 0.5% |

-continued

| Recipe | 25a | 25b |
|---|---|---|
| Water | to 100% | to 100% |
| Glycerin | 3.0% | 3.0% |
| Phenoxyethanol; Ethylhexylglycerin (Euxyl PE 9010, Schülke & Mayr GmbH) | 0.7% | |
| Ethanol | 5.0% | 5.0% |
| Glyceryl Caprylate (dermosoft ® GMC; Evonik Dr. Straetmans GmbH) | | 0.4% |
| Zinc Sulfate | | 1.0% |

Recipes 26a and 26b: W/O Cream

| Recipe | 26a | 26b |
|---|---|---|
| Composition from example 5 | 2.0% | 2.0% |
| Mineral oil | 17.0% | 17.0% |
| Castor wax | 0.4% | 0.4% |
| Microcrystalline Wax | 0.6% | 0.6% |
| Water | to 100% | to 100% |
| Sodium Chloride | 0.5% | 0.5% |
| Urea | 10.0% | 10.0% |
| Phenoxyethanol; Ethylhexylglycerin (Euxyl PE 9010, Schülke & Mayr GmbH) | 0.7% | |
| Glyceryl Caprylate (dermosoft ® GMC; Evonik Dr. Straetmans GmbH) | | 0.35% |
| Pentylene Glycol (dermosoft ® Pentiol eco; Evonik Dr. Straetmans GmbH) | | 2.0% |

Recipes 27a and 27b: Quick-Breaking Cream

| Recipe | 27a | 27b |
|---|---|---|
| Composition from example 5 | 0.8% | 0.8% |
| Cetyl Dimethicone (ABIL ® Wax 9801, Evonik Operations GmbH) | 1.6% | 1.6% |
| Diethylhexyl Carbonate (TEGOSOFT ® DEC, Evonik Operations GmbH) | 4.0% | 4.0% |
| Dimethicone (ABIL ® 350, Evonik Operations GmbH) | 1.0% | 1.0% |
| Cyclopentasiloxane | 4.0% | 4.0% |
| Magnesium Stearate | 0.3% | 0.3% |
| Water | to 100% | to 100% |
| Propylene Glycol | 5.0% | 5.0% |
| Sodium Chloride | 1.0% | 1.0% |
| Methylisothiazolinone, Methylparaben, Ethylparaben; Dipropylene Glycol (Microcare MEM, Thor) | 0.8% | |
| Glyceryl Caprylate (dermosoft ® GMC; Evonik Dr. Straetmans GmbH) | | 0.25% |
| Phenylpropanol (dermosoft ® 250 eco; Evonik Dr. Straetmans GmbH) | | 0.35% |

Recipes 28a, 26b and 28c: Cooing Body Lotion

| Recipe | 28a | 28b | 28c |
|---|---|---|---|
| Composition from example 5 | 2.0% | 1.5% | 1.5% |
| Polyglyceryl-4 Diisostearate/Polyhydroxystearate/Sebacate (ISOLAN ® GPS, Evonik Operations GmbH) | — | 0.5% | 0.5% |
| Castorwax | 0.5% | 0.5% | 0.5% |
| Beeswax | 0.5% | 0.5% | 0.5% |
| Ethylhexyl Stearate (TEGOSOFT ® OS, Evonik Operations GmbH) | 10.0% | 10.0% | 10.0% |
| Diethylhexyl Carbonate (TEGOSOFT ® DEC, Evonik Operations GmbH) | 8.5% | 8.5% | 8.5% |
| Dimethicone (Belsil DM 5, Wacker Chemical Corp.) | 6.0% | 6.0% | 6.0% |
| Tocopheryl Acetate | 0.5% | 0.5% | 0.5% |
| Glycerin | 3.0% | 3.0% | 3.0% |
| Water | to 100% | to 100% | to 100% |
| Sodium Chloride | 1.0% | 1.0% | 1.0% |
| Ethanol | 20.0% | 20.0% | 20.0% |
| Ethylhexylglycerin (dermosoft ® EHG; Evonik Dr. Straetmans GmbH) | | | 0.5% |

Recipes 29a, 29b and 29c: W/O Cream Based on Natural Ingredients

| Recipe | 29a | 29b | 29c |
|---|---|---|---|
| Composition from example 5 | 3.0% | 2.5% | 2.5% |
| Diisostearoyl Polyglyceryl-3 Dimer Dilinoleate (ISOLAN ® PDI, Evonik Operations GmbH) | — | 0.5% | 0.5% |
| Diethylhexyl Carbonate (TEGOSOFT ® DEC, Evonik Operations GmbH) | 7.0% | 7.0% | 7.0% |
| Oleyl Erucate (TEGOSOFT ® OER, Evonik Operations GmbH) | 3.0% | 3.0% | 3.0% |
| Almond oil | 7.0% | 7.0% | 7.0% |
| Shea butter | 2.0% | 2.0% | 2.0% |
| Cetyl Ricinoleate (TEGOSOFT ® CR, Evonik Operations GmbH) | 1.0% | 1.0% | 1.0% |
| Beeswax | 0.6% | 0.6% | 0.6% |
| Castor wax | 0.4% | 0.4% | 0.4% |
| Glycerin | 5.0% | 5.0% | 5.0% |
| Water | to 100% | to 100% | to 100% |
| Magnesium sulfate heptahydrate | 1.5% | 1.5% | 1.5% |
| Sodium Benzoate, Potassium Sorbate (Euxyl K 712, Schülke & Mayr GmbH) | 0.5% | 0.5% | |
| Pentylene Glycol (dermosoft ® Pentiol eco; Evonik Dr. Straetmans GmbH) | | | 3.0% |

Recipes 30a, 30b and 30c: Cold-Preparable Lotion

| Recipe | 30a | 30b | 30c |
|---|---|---|---|
| Composition from example 5 | 3.0% | 2.5% | 2.5% |
| Polyglyceryl-3 Oleate (ISOLAN ® GO 33, Evonik Operations GmbH) | — | 0.5% | 0.5% |
| Isoamyl Cocoate (TEGOSOFT ® AC, Evonik Operations GmbH) | 5.0% | 5.0% | 5.0% |
| Diethylhexyl Carbonate (TEGOSOFT ® DEC, Evonik Operations GmbH) | 12.0% | 12.0% | 12.0% |
| Phenoxyethyl Caprylate (TEGOSOFT ® XC, Evonik Operations GmbH) | 4.0% | 4.0% | 4.0% |
| Zinc Stearate | 0.5% | 0.5% | 0.5% |
| Water | to 100% | to 100% | to 100% |
| Glycerin | 3.0% | 3.0% | 3.0% |
| Sodium Chloride | 1.5% | 1.5% | 1.5% |
| Phenoxyethanol; Ethylhexylglycerin (Euxyl PE 9010, Schülke & Mayr GmbH) | 0.7% | 0.7% | |
| Benzyl Alcohol; Caprylyl Glycol; Benzoic Acid (VERSTATIL ® BOB; Evonik Dr. Straetmans GmbH) | | | 1.5% |

Recipes 31a, 31 b and 31c: Moisturizing Lotion Containing Urea

| Recipe | 31a | 31b | 31c |
|---|---|---|---|
| Composition from example 5 | 2.0% | 1.5% | 1.5% |
| Cetyl PEG/PPG-10/1 Dimethicone (ABIL ® EM 180, Evonik Operations GmbH) | — | 0.5% | 0.5% |
| Microcrystalline Wax | 0.5% | 0.5% | 0.5% |
| Castor wax | 0.5% | 0.5% | 0.5% |
| C12-15 Alkyl Benzoate | 7.5% | 7.5% | 7.5% |
| Oleyl Erucate (TEGOSOFT ® OER, Evonik Operations GmbH) | 5.0% | 5.0% | 5.0% |
| Ethylhexyl Palmitate (TEGOSOFT ® OP, Evonik Operations GmbH) | 5.0% | 5.0% | 5.0% |
| Caprylic/Capric Triglyceride | 5.0% | 5.0% | 5.0% |
| Glycerin | 3.0% | 3.0% | 3.0% |
| Urea | 20.0% | 20.0% | 20.0% |

-continued

| Recipe | 31a | 31b | 31c |
|---|---|---|---|
| Magnesium sulfate heptahydrate | 1.0% | 1.0% | 1.0% |
| Water | to 100% | to 100% | to 100% |
| Phenoxyethanol; Ethylhexylglycerin (Euxyl PE 9010, Schülke & Mayr GmbH) | 0.70% | 0.70% | |
| Parfum | 0.10% | 0.10% | 0.10% |
| Methylpropanediol; Phenoxyethanol; Caprylyl Glycol (VERSTATIL ® MFC; Evonik Dr. Straetmans GmbH) | | | 1.5% |

Recipes 32a 32b 32c and 32d: W/O Lotion with Light-as-Silk Skin Feel

| Recipe | 32a | 32b | 32c | 33d |
|---|---|---|---|---|
| Composition from example 5 | 2.5% | 2.0% | 2.0% | 2.0% |
| Cetyl PEG/PPG-10/1 Dimethicone (ABIL ® EM 90, Evonik Operations GmbH) | — | 0.5% | — | — |
| Bis-PEG/PPG-14/14 Dimethicone; Dimethicone (ABIL ® EM 97 S, Evonik Operations GmbH) | — | — | 1.0% | 1.0% |
| Microcrystalline Wax | 0.1% | 0.1% | 0.1% | 0.1% |
| Castor wax | 0.1% | 0.1% | 0.1% | 0.1% |
| Diethylhexyl Carbonate (TEGOSOFT ® DEC, Evonik Operations GmbH) | 11.8% | 11.8% | 11.8% | 11.8% |
| Myristyl Myristate (TEGOSOFT ® MM, Evonik Operations GmbH) | 1.0% | 1.0% | 1.0% | 1.0% |
| Dimethicone (Belsil DM 5, Wacker Chemical Corp.) | 8.0% | 8.0% | 8.0% | 8.0% |
| Dimethicone (ABIL ® 350, Evonik Operations GmbH) | 0.5% | 0.5% | 0.5% | 0.5% |
| Glycerin | 3.0% | 3.0% | 3.0% | 3.0% |
| Magnesium sulfate heptahydrate | 1.5% | 1.5% | 1.5% | 1.5% |
| Water | to 100% | to 100% | to 100% | to 100% |
| Benzyl Alcohol; Ethylhexylglycerin; Tocopherol (Euxyl K 900, Schülke & Mayr GmbH) | 0.7% | 0.7% | 0.7% | |
| Phenoxyethanol; Ethylhexylglycerin (VERSTATIL ® PE; Evonik Dr. Straetmans GmbH) | | | | 1.0% |

Recipes 33a, 33b and 33c: Baby-Care Product

| Recipe | 33a | 33b | 33c |
|---|---|---|---|
| Composition from example 5 | 3.0% | 2.0% | 2.0% |
| Paraffinum Liquidum; Petrolatum; Ozokerite; Glyceryl Oleate; Lanolin Alcohol (PROTEGIN ® XN, Evonik Operations GmbH) | — | 1.0% | 1.0% |
| Castor wax | 0.1% | 0.1% | 0.1% |
| Microcrystalline Wax | 0.1% | 0.1% | 0.1% |
| Oleyl Erucate (TEGOSOFT ® OER, Evonik Operations GmbH) | 1.0% | 1.0% | 1.0% |
| Isoamyl Cocoate (TEGOSOFT ® AC, Evonik Operations GmbH) | 3.8% | 3.8% | 3.8% |
| Ethylhexyl Palmitate (TEGOSOFT ® OP, Evonik Operations GmbH) | 1.0% | 1.0% | 1.0% |
| Almond oil | 1.0% | 1.0% | 1.0% |
| Zinc Oxide | 20.0% | 20.0% | 20.0% |
| Glycerin | 3.0% | 3.0% | 3.0% |
| Magnesium sulfate heptahydrate | 1.0% | 1.0% | 1.0% |
| Sodium Lactate; Sodium PCA; Glycine; Fructose; Urea; Niacinamide; Inositol; Sodium Benzoate; Lactic Acid (LACTIL, Evonik Operations GmbH) | 5.0% | 5.0% | 5.0% |
| Betaine (TEGO ® Natural Betaine, Evonik Operations GmbH) | 3.0% | 3.0% | 3.0% |
| Water | to 100% | to 100% | to 100% |
| Benzyl Alcohol; Ethylhexylglycerin; Tocopherol (Euxyl K 900, Schülke & Mayr GmbH) | 0.7% | 0.7% | |
| p-Anisic Acid (dermosoft ® 688; Evonik Dr. Straetmans GmbH) | | | 0.12% |
| Pentylene Glycol (dermosoft ® Pentiol eco; Evonik Dr. Straetmans GmbH) | | | 2.5% |

Recipe 34a, 34b and 34c: Foot-Care Product

| Recipe | 34a | 34b | 34c |
|---|---|---|---|
| Composition from example 5 | 3.0% | 2.5% | 2.5% |
| Petrolatum; Ozokerite; Hydrogenated Castor Oil; Glyceryl Isostearate; Polyglyceryl-3 Oleate (PROTEGIN ® W, Evonik Operations GmbH) | — | 0.5% | 0.5% |
| Castor wax | 0.1% | 0.1% | 0.1% |
| Microcrystalline Wax | 0.1% | 0.1% | 0.1% |
| Diethylhexyl Carbonate (TEGOSOFT ® DEC, Evonik Operations GmbH) | 9.0% | 9.0% | 9.0% |
| Ethylhexyl Palmitate (TEGOSOFT ® OP, Evonik Operations GmbH) | 9.0% | 9.0% | 9.0% |
| Stearyl Heptanoate (TEGOSOFT ® SH, Evonik Operations GmbH) | 8.8% | 8.8% | 8.8% |
| Glycerin | 3.0% | 3.0% | 3.0% |
| Magnesium sulfate heptahydrate | 1.0% | 1.0% | 1.0% |
| Ceramide NP; Ceramide AP; Ceramide EOP; Phytosphingosine; Cholesterol; Sodium Lauroyl Lactylate; Carbomer; Xanthan Gum (SK-INFLUX V, Evonik Operations GmbH) | 5.0% | 5.0% | 5.0% |
| Betaine (TEGO ® Natural Betaine, Evonik Operations GmbH) | 3.0% | 3.0% | 3.0% |
| Water | to 100% | to 100% | to 100% |
| Benzyl Alcohol; Ethylhexylglycerin; Tocopherol (Euxyl K 900, Schülke & Mayr GmbH) | 0.7% | 0.7% | |
| Phenoxyethanol; Benzoic Acid (Verstatil ® BP; Evonik Dr. Straetmans GmbH) | | | 1.0% |

Recipes 35a and 35b: Sunscreen Lotion SPF 30 UVA with Insect Repellent

| Recipe | 35a | 35b |
|---|---|---|
| Composition from example 5 | 3.0% | 2.0% |
| Polyglyceryl-2 Dipolyhydroxystearate (Dehymuls PGPH, BASF SE) | — | 1.0% |
| Oleyl Erucate (TEGOSOFT ® OER, Evonik Operations GmbH) | 1.5% | 1.5% |
| Diethylhexyl Carbonate (TEGOSOFT ® DEC, Evonik Operations GmbH) | 1.5% | 1.5% |
| Diethylamino Hydroxybenzoyl Hexyl Benzoate (Uvinul A Plus, BASF SE) | 5.4% | 5.4% |
| Ethylhexyl Methoxycinnamate | 10.0% | 10.0% |
| Octocrylene | 2.0% | 2.0% |
| Polyacrylamide; C13-14 Isoparaffin; Laureth-7 (Sepigel 305, Seppic) | 2.1% | 2.1% |
| Ethyl Butylacetylaminopropionate (R3535, Merck KGaA) | 4.0% | 4.0% |
| Tocopheryl Acetate | 0.5% | 0.5% |
| Glycerin | 3.0% | 3.0% |
| Ethanol | 0.5% | 0.5% |
| Magnesium sulfate heptahydrate | 1.0% | 1.0% |
| Water | to 100% | to 100% |
| Benzyl Alcohol; Ethylhexylglycerin; Tocopherol (Euxyl K 900, Schülke & Mayr GmbH) | 0.7% | 0.7% |
| Parfum | 0.1% | 0.1% |

Recipes 36a and 36b: Sunscreen Lotion SPF 30 UVA in Accordance with Ecocert Criteria

| Recipe | 36a | 36b |
|---|---|---|
| Composition from example 5 | 3.0% | 2.0% |
| Polyglyceryl-3 Polyricinoleate (Cithrol PG3PR, (Croda Int. Plc) | — | 1.0% |
| Isoamyl Cocoate (TEGOSOFT ® AC, Evonik Operations GmbH) | 2.0% | 2.0% |
| Decyl Cocoate (TEGOSOFT ® DC, Evonik Operations GmbH) | 10.0% | 10.0% |
| Isopropyl Palmitate (TEGOSOFT ® P, Evonik Operations GmbH) | 10.0% | 10.0% |
| Zinc Oxide (Zinc Oxide PI, Symrise) | 16.0% | 16.0% |
| Titanium Dioxide (nano); Alumina; Stearic Acid (EusolexT-S, Merck KGaA) | 9.0% | 9.0% |
| Water | to 100% | to 100% |
| Glycerin | 3.0% | 3.0% |
| Magnesium sulfate heptahydrate | 1.0% | 1.0% |
| Sodium Benzoate, Potassium Sorbate (Euxyl K 712, Schülke & Mayr GmbH) | 0.5% | 0.5% |

Recipes 37a 37b 37c and 37d: Sunscreen SPF 30 UVA

| Recipe | 37a | 37b | 37c | 37d |
|---|---|---|---|---|
| Composition from example 5 | 3.0% | 2.0% | 3.0% | 2.0% |
| Cetyl PEG/PPG-10/1 Dimethicone (ABIL ® EM 90, Evonik Operations GmbH) | — | 1.0% | — | — |
| Polyglyceryl-4 Diisostearate/Polyhydroxystearate/Sebacate (ISOLAN ® GPS, Evonik Operations GmbH) | — | — | — | 1.0% |
| Diethylhexyl Carbonate (TEGOSOFT ® DEC, Evonik Operations GmbH) | 13.0% | 13.0% | 11.3% | 11.3% |
| C12-15 Alkyl Benzoate | 13.0% | 13.0% | 11.3% | 11.3% |
| Bis-Ethylhexyloxyphenol Methoxyphenyl Triazine (Tinosorb S, BASF SE) | 1.0% | 1.0% | 1.5% | 1.5% |
| Butyl Methoxydibenzoylmethane | — | — | 3.0% | 3.0% |
| Ethylhexyl Methoxycinnamate | 5.0% | 5.0% | | |
| Octocrylene | — | — | 6.0% | 6.0% |
| Homosalate | — | — | 4.0% | 4.0% |
| Diethylamino Hydroxybenzoyl Hexyl Benzoate (Uvinul A Plus, BASF SE) | 5.0% | 5.0% | — | — |
| Water | to 100% | to 100% | to 100% | to 100% |
| Glycerin | 3.0% | 3.0% | 3.0% | 3.0% |
| Magnesium sulfate heptahydrate | 1.0% | 1.0% | 1.0% | 1.0% |
| UV filter solution (20% Phenylbenzimidazole Sulfonic Acid (Eusolex 232, Merck KGaA, 8.8% tris(hydroxymethyl)aminomethane, water to 100%) | 15.0% | 15.0% | 15.0% | 15.0% |
| Benzyl Alcohol; Ethylhexylglycerin; Tocopherol (Euxyl K 900, Schülke & Mayr GmbH) | 0.7% | 0.7% | 0.7% | 0.7% |

Recipes 38a, 38b, 38c and 38d: Sunscreen Lotion SPF 50 UVA

| Recipe | 38a | 38b | 38c | 38d |
|---|---|---|---|---|
| Composition from example 5 | 3.0% | 2.5% | 3.0% | 2.5% |
| Cetyl PEG/PPG-10/1 Dimethicone (ABIL ® EM 90, Evonik Operations GmbH) | — | 1.0% | — | 1.0% |
| Microcrystalline Wax | 0.3% | 0.3% | 0.3% | 0.3% |
| Castor wax | 0.3% | 0.3% | 0.3% | 0.3% |
| Diethylhexyl Carbonate (TEGOSOFT ® DEC, Evonik Operations GmbH) | 2.4% | 2.4% | — | — |
| Phenoxyethyl Caprylate (TEGOSOFT ® XC, Evonik Operations GmbH) | — | — | 3.9% | 3.9% |
| Bis-Ethylhexyloxyphenol Methoxyphenyl Triazine (Tinosorb S, BASF SE) | 6.0% | 6.0% | — | — |
| Diethylamino Hydroxybenzoyl Hexyl Benzoate (Uvinul A Pius, BASF SE) | 7.0% | 7.0% | 5.0% | 5.0% |
| Butyl Methoxydibenzoylmethane | — | — | 4.5% | 4.5% |
| Ethylhexyl Salicylate | 3.0% | 3.0% | 5.0% | 5.0% |
| Ethylhexyl Methoxycinnamate | 7.0% | 7.0% | — | — |
| Octocrylene | — | — | 9.0% | 9.0% |
| Homosalate | 3.0% | 3.0% | 5.0% | 5.0% |
| Ethylhexyl Triazone (Uvinul T 150, BASF SE) | 1.0% | 1.0% | 2.0% | 2.0% |
| Titanium Dioxide; silica; Dimethicone (Parsol TX (DSM Nutritional Products Llc.) | 2.0% | 2.0% | 2.0% | 2.0% |
| Water | to 100% | to 100% | to 100% | to 100% |
| Glycerin | 3.0% | 3.0% | 3.0% | 3.0% |
| Magnesium sulfate heptahydrate | 1.5% | 1.5% | 1.5% | 1.5% |
| Benzyl Alcohol; Ethylhexylglycerin; Tocopherol (Euxyl K 900, Schülke & Mayr GmbH) | 0.7% | 0.7% | 0.7% | |
| Phenethylalcohol nat. | | | | 0.7% |

Recipes 39a, 39b and 39c: Sunscreen Lotion SPF 50 in Accordance with FDA Criteria

| Recipe | 39a | 39b | 39c |
|---|---|---|---|
| Composition from example 5 | 2.0% | 1.5% | 1.5% |
| Lauryl PEG-10 Tris(Trimethylsiloxy)Silylethyl Dimethicone (ES-5300 Formulation Aid, Dow Corning Corp.) | — | 0.5% | 0.5% |
| Ethylhexyl Methoxycinnamate; Diethylamino Hydroxybenzoyl Hexyl Benzoate (Uvinul A + B, BASF SE) | 7.5% | 7.5% | 7.5% |
| Ethylhexyl Salicylate | 5.0% | 5.0% | 5.0% |
| Homosalate | 15.0% | 15.0% | 15.0% |
| Butyl Methoxydibenzoylmethane | 3.0% | 3.0% | 3.0% |
| Benzophenone-3 | 6.0% | 6.0% | 6.0% |
| Octocrylene | 10.0% | 10.0% | 10.0% |
| Triisostearin | 2.0% | 2.0% | 2.0% |

-continued

| Recipe | 39a | 39b | 39c |
|---|---|---|---|
| Microcrystalline Wax | 1.2% | 1.2% | 1.2% |
| Castor wax | 0.8% | 0.8% | 0.8% |
| Cetyl Dimethicone (ABIL ® Wax 9801, Evonik Operations GmbH) | 2.0% | 2.0% | 2.0% |
| Diethylhexyl Carbonate (TEGOSOFT ® DEC, Evonik Operations GmbH) | 2.0% | 2.0% | 2.0% |
| Water | to 100% | to 100% | to 100% |
| Sodium Chloride | 1.0% | 1.0% | 1.0% |
| Ethylenediaminetetraacetic acid | 0.1% | 0.1% | 0.1% |
| Propylene glycol | 3.0% | 3.0% | 3.0% |
| Phenoxyethanol; Ethylhexylglycerin (Euxyl PE 9010, Schülke & Mayr GmbH) | 0.7% | 0.7% | |
| Verstatil PC | | | 1.0% |

Recipe 40a, 40b, 40c, 40d, 40e, and 40f: Foundation

| Recipe | 40a | 40b | 40c | 40d | 40e | 40f |
|---|---|---|---|---|---|---|
| Composition from example 5 | 4.5% | 2.5% | 3.0% | 2.5% | 2.0% | 2.0% |
| Bis-(Glyceryl/Lauryl) Glyceryl Lauryl Dimethicone; Caprylic/Capric Triglyceride (ABIL ® EM 120, Evonik Operations GmbH) | — | 2.0% | — | — | — | — |
| Polyglyceryl-4 Isostearate (ISOLAN ®) GI 34, Evonik Operations GmbH) | — | — | 1.0% | — | — | — |
| Cetyl Diglyceryl Tris(Trimethylsiloxy)Silylethyl Dimethicone (DC-5600, Dow Corning Corp.) | — | — | — | 1.0% | — | — |
| Lauryl Polyglycery-3 Polydimethyisiloxyethyl Dimethicone (KF-6105, Shin-Etsu Chemical Co.) | — | — | — | — | 1.0% | — |
| Polyglyceryl-4 isostearate; Cetyl PEG/PPG-10/1 Dimethicone; Hexyl Laurate (ABIL ® WE 09, Evonik Operations GmbH) | — | — | — | — | — | 2.0% |
| Isoamyl Cocoate (TEGOSOFT ® AC, Evonik Operations GmbH) | 10.8% | 10.8% | 10.8% | 10.8% | 10.8% | 10.8% |
| Oleyl Erucate (TEGOSOFT ® OER, Evonik Operations GmbH) | 8.0% | 8.0% | 8.0% | 8.0% | 8.0% | 8.0% |
| Titanium Dioxide, Alumina, Triethoxycaprylyisilane (Hombitan AC360, Sachtleben) | 4.0% | 4.0% | 4.0% | 4.0% | 4.0% | 4.0% |
| Iron Oxides (Sicovit Brown 70 E 172, Rockwood) | 2.1% | 2.1% | 2.1% | 2.1% | 2.1% | 2.1% |
| Nylon-12 (TEGOLON ® 12-20, Evonik Operations GmbH) | 2.0% | 2.0% | 2.0% | 2.0% | 2.0% | 2.0% |
| Cyclopentasiloxane | 3.5% | 3.5% | 3.5% | 3.5% | 3.5% | 3.5% |
| Disteardimonium Hectorite (Bentone 38 V CG, Elementis) | 1.0% | 1.0% | 1.0% | 1.0% | 1.0% | 1.0% |
| Propylene carbonate | 0.5% | 0.5% | 0.5% | 0.5% | 0.5% | 0.5% |
| Water | to 100% | to 100% | to 100% | to 100% | to 100% | to 100% |
| Magnesium sulfate heptahydrate | 1.5% | 1.5% | 1.5% | 1.5% | 1.5% | 1.5% |
| Glycerin | 5.0% | 5.0% | 5.0% | 5.0% | 5.0% | 5.0% |
| Creatine (TEGO ® Cosmo C 100, Evonik Operations GmbH) | 0.5% | 0.5% | 0.5% | 0.5% | 0.5% | 0.5% |
| Ceteareth-25; Glycerin; Cetyl Alcohol; Behenic Acid; Cholesterol; Ceramide EOP; Ceramide EOS; Ceramide NP; Ceramide NS; Ceramide AP; Caprooyl Phytosphingosine; Caprooyl Sphingosine (SKINMIMICS, Evonik Operations GmbH) | | | | | | |
| Benzyl Alcohol; Ethylhexylglycerin; Tocopherol (Euxyl K 900, Schülke & Mayr GmbH) | 0.7% | 0.7% | 0.7% | 0.7% | 0.7% | 0.7% |

Recipe 41a, 41b, 41c, 41d, 41e, 41f, and 41g: CC (Colour Control) Fluid

| Recipe | 41a | 41b | 41c | 41d | 41e | 41f | 41g |
|---|---|---|---|---|---|---|---|
| Composition from example 5 | 3.0% | 2.0% | 2.5% | 3.0% | 2.5% | 2.0% | 1.0% |
| Polyglyceryl-4 Diisostearate/Polyhydroxystearate/Sebacate (ISOLAN ® GPS, Evonik Operations GmbH) | — | 1.0% | — | — | — | — | — |
| Sorbitan Oleate (TEGO ® SMO V, Evonik Operations GmbH) | — | — | 0.5% | — | — | — | — |
| PEG-30 Dipolyhydroxystearate (Arlacel P135, Croda) | — | — | — | 1.0% | — | — | — |
| Polyglyceryl-3 Diisostearate (Lameform TGI, BASF SE) | — | — | — | — | 1.5% | — | — |
| Glyceryl Oleate, Polyglyceryl-3 Polyricinoleate, *Olea Europaea* (olive) Oil Unsaponifiables (Plantasens Natural Emulsifier CP5, Clariant) | — | — | — | — | — | 1.0% | — |
| Lauryl PEG-9 Polydimethylsiloxyethyl Dimethicone (KF-6038, Shin-Etsu Chemical Co.) | — | — | — | — | — | — | 1.0% |
| Ethylhexyl Methoxycinnamate; Diethylamino Hydroxybenzoyl Hexyl Benzoate (Uvinul A + B, BASF SE) | 10.0% | 10.0% | 10.0% | 10.0% | 10.0% | 10.0% | 10.0% |
| Cyclopentasiloxane | 3.5% | 3.5% | 3.5% | 3.5% | 3.5% | 3.5% | 3.5% |
| Disteardimonium Hectorite (Bentone 38 V CG, Elementis) | 1.0% | 1.0% | 1.0% | 1.0% | 1.0% | 1.0% | 1.0% |
| Propylene carbonate | 0.5% | 0.5% | 0.5% | 0.5% | 0.5% | 0.5% | 0.5% |
| Titanium Dioxide, Alumina, Triethoxycaprylylsilane (Hombitan AC360, Sachtleben) | 4.0% | 4.0% | 4.0% | 4.0% | 4.0% | 4.0% | 4.0% |
| Talc | 2.0% | 2.0% | 2.0% | 2.0% | 2.0% | 2.0% | 2.0% |
| Iron Oxides; Triethoxycaprylylsilane (Unipure Yellow LC 182 AS-EM, Sensient) | 0.4% | 0.4% | 0.4% | 0.4% | 0.4% | 0.4% | 0.4% |
| Iron Oxides; Triethoxycaprylylsilane (Unipure Red LC 381 AS-EM, Sensient) | 0.12% | 0.12% | 0.12% | 0.12% | 0.12% | 0.12% | 0.12% |
| Iron Oxides; Triethoxycaprylylsilane (Unipure Black LC 989 AS-EM, Sensient) | 0.08% | 0.08% | 0.08% | 0.08% | 0.08% | 0.08% | 0.08% |
| Diethylhexyl Carbonate (TEGOSOFT ® DEC, Evonik Operations GmbH) | 4.0% | 4.0% | 4.0% | 4.0% | 4.0% | 4.0% | 4.0% |
| C12-15 Alkyl Benzoate | 4.0% | 4.0% | 4.0% | 4.0% | 4.0% | 4.0% | 4.0% |
| Isopropyl Palmitate (TEGOSOFT ® P, Evonik Operations GmbH) | 4.0% | 4.0% | 4.0% | 4.0% | 4.0% | 4.0% | 4.0% |
| Nylon-12 (TEGOLON ® 12-20, Evonik Operations GmbH) | 2.0% | 2.0% | 2.0% | 2.0% | 2.0% | 2.0% | 2.0% |
| Water | to 100% | to 100% | to 100% | to 100% | to 100% | to 100% | to 100% |
| Glycerin | 5.0% | 5.0% | 5.0% | 5.0% | 5.0% | 5.0% | 5.0% |
| Sodium Chloride | 1.5% | 1.5% | 1.5% | 1.5% | 1.5% | 1.5% | 1.5% |
| Tetrapeptide-30; Glycerin (TEGO ® Pep 4-Even, Evonik Operations GmbH) | 0.3% | 0.3% | 0.3% | 0.3% | 0.3% | 0.3% | 0.3% |
| Phenoxyethanol; Methylparaben; Ethylparaben; Propylparaben (Phenonip XB, Clariant) | 0.7% | 0.7% | 0.7% | 0.7% | 0.7% | 0.7% | 0.7% |

Recipe 42a 42b 42c 42d and 42e: Antiperspirant/Deodorant Spray or Aerosol Spray

| Recipe | 42a | 42b | 42c | 42d | 42e |
|---|---|---|---|---|---|
| Composition from example 5 | 3.0% | 2.0% | 3.0% | 2.0% | 2.0% |
| Polyglyceryl-4 Diisostearate/Polyhydroxystearate/Sebacate (ISOLAN ® GPS, Evonik Operations GmbH) | — | 1.0% | — | 1.0% | 1.0% |
| Isopropyl Palmitate (TEGOSOFT ® P, Evonik Operations GmbH) | 20.0% | 20.0% | 20.0% | 20.0% | 20.0% |
| Diethylhexyl Carbonate (TEGOSOFT ® DEC, Evonik Operations GmbH) | 7.0% | 7.0% | 7.0% | 7.0% | 7.0% |
| Triethyl Citrate (dermofeel ® TEC eco; Evonik Dr. Straetmans GmbH) | | | | | 5.0% |
| Water | to 100% | to 100% | to 100% | to 100% | to 100% |
| Glycerin | 2.0% | 2.0% | 2.0% | 2.0% | 2.0% |

-continued

| Recipe | 42a | 42b | 42c | 42d | 42e |
|---|---|---|---|---|---|
| Aluminum Chlorohydrate (50% aq.; Locron LIC, Clariant AG) | 30.0% | 30.0% | 30.0% | 30.0% | 30.0% |
| Parfum | 1.0% | 1.0% | 1.0% | 1.0% | 1.0% |
| Propellant | — | — | Mix emulsions 42c and 42d with propellant in mass ratio of 5:2 | | |
| Phenoxyethanol; Caprylyl Glycol (Vestatil ® PC; Evonik Dr. Straetmans GmbH) | | | | | 0.8% |

Recipe 43a, 43b, 43c, and 43d: Sunscreen aerosol SPF 50 UVA

| Recipe | 43a | 43b | 43c | 43d |
|---|---|---|---|---|
| Composition from example 5 | 4.0% | 4.0% | 4.0% | 4.0% |
| Cetyl PEG/PPG-10/1 Dimethicone (ABIL ® EM 90, Evonik Operations GmbH) | — | — | 1.0% | 1.0% |
| C12-15 Alkyl Benzoate | 10.0% | 8.0% | 10.0% | 8.0% |
| Diethylhexyl Carbonate (TEGOSOFT ® DEC, Evonik Operations GmbH) | 13.0% | 10.0% | 13.0% | 10.0% |
| Bis-Ethylhexyloxyphenol Methoxyphenyl Triazine (Tinosorb S, BASF SE) | 4.0% | 4.0% | 4.0% | 4.0% |
| Diethylamino Hydroxybenzoyl Hexyl Benzoate (Uvinul A Plus, BASF SE) | 5.0% | 5.0% | 5.0% | 5.0% |
| Ethylhexyl Salicylate | 5.0% | 5.0% | 5.0% | 5.0% |
| Ethylhexyl Methoxycinnamate | 4.0% | 4.0% | 4.0% | 4.0% |
| Water | to 100% | to 100% | to 100% | to 100% |
| Glycerin | 3.0% | 3.0% | 3.0% | 3.0% |
| UV filter solution (20% Phenylbenzimidazole Sulfonic Acid (Eusolex 232, Merck KGaA, 8.8% tris(hydroxymethyl)aminomethane, water to 100%) | 20.0% | 20.0% | 20.0% | 20.0% |
| Magnesium sulfate heptahydrate | 1.0% | 1.0% | 1.0% | 1.0% |
| Benzyl Alcohol; Ethylhexylglycerin; Tocopherol (Euxyl K 900, Schülke & Mayr GmbH) | 0.7% | 0.7% | 0.7% | 0.7% |
| Mix emulsions 43a, 43b, 43c and 43d with propellant in mass ratio of 2:11 | | | | |

Formulation 44: Shower Cream

| | |
|---|---|
| Water | to 100.0% |
| Composition from example 1, 2 or 3 | 1.5% |
| Sodium Laureth Sulfate (Texapon NSO, BASF, 28%) | 25.0% |
| Coco-Glucoside (Plantacare 818 UP, BASF, 51%) | 8.0% |
| Cocamidopropyl Betaine (TEGO ® Betain F 50, Evonik, 38%) | 8.0% |
| PEG-18 Glyceryl Oleate/Cocoate (ANTIL ® 171, Evonik) | 1.5% |
| Sorbitan Sesquicaprylate (ANTIL ® Soft SC, Evonik) | 0.8% |
| Glyceryl Oleate (TEGIN ® O V, Evonik) | 0.8% |
| Perfume Spicy Herbs (IFF) | 0.2% |
| Polyglyceryl-4 Caprate (TEGOSOFT ® PC 41, Evonik) | 0.6% |
| Hellanthus Annuus Seed Oil (AEC Sunflower Oil, A & E Connock, Perfumery & Cosmetics Ltd.) | 0.2% |
| Linalool (Lipofresh, Lipo Chemicals, Inc.) | 0.1% |
| Coumarin (Rhodiascent extra pure, Solvay Rhodia) | 0.1% |
| Glycerin (Glycerol EP, vegetable, Spiga Nord) | 0.4% |
| Hydroxypropyl Methylcellulose (TEGOCEL ® HPM 50, Evonik) | 0.2% |
| Glycol Distearate (TEGIN ® G 1100 Pellets, Evonik) | 0.4% |
| Sodium Chloride | 0.5% |
| Hydroxypropyl Guar Hydroxypropyltrimonium Chloride (Jaguar C-162, Solvay Rhodia) | 0.2% |
| dermofeel TOCO 70 non GMO | 0.1% |
| Disodium EDTA (Dissolvine NA-2-P, AkzoNobel) | 0.1% |
| Preservative | q.s. |
| Citric Acid | to pH 5.2 |

Formulation 45: Bogy Shampoo

| | | |
|---|---|---|
| phase A | Composition from example 1, 2 or 3 | 5.0% |
| | Lavandula Angustifolia (lavender) Oil (AEC Lavender Oil, A & E Connock Ltd.) | 0.2% |
| | Perfume | 0.1% |
| Phase B | Sodium Cocoamphoacetate (REWOTERIC ® AM C, Evonik, 32%) | 10.0% |
| Phase C | Water | to 100.0% |
| | Xanthan Gum (Keitrol CG-SFT, CP Kelco) | 1.2% |
| Phase D | Sodium Lauroyl Methyl Isethionate (Iselux, Innospec Active Chemicals) | 4.5% |
| | Capryl/Capramidopropyl Betaine (TEGO ® Betaine 810, Evonik, 38%) | 4.5% |
| | Citric Acid | 1.2% |
| Phase E | Water | 10.0% |
| | Polyquaternium-7 (Merquat 550, Nalco) | 0.4% |
| | Preservative | q.s. |

Formulation 46: Shampoo

| | | |
|---|---|---|
| Phase A | Composition from example 1, 2 or 3 | 3.5% |
| | Isopropyl Myristate (TEGOSOFT ® M, Evonik) | 0.2% |
| | Perfume | 0.1% |

-continued

| | | |
|---|---|---|
| Phase B | Water | to 100.0% |
| Phase C | Sodium Lauryl Sulfate (Texapon LS 35, BASF, 30%) | 28.0% |
| Phase D | Cocamidopropyl Betaine (TEGO ® Betain F 50, Evonik, 38%) | 9.0% |
| Phase E | Cocamide MEA (REWOMID ® C 212, Evonik) | 2.0% |
| | Xanthan Gum (Keltrol CG-SFT, CP Kelco) | 0.3% |
| | Water | 10.0% |

-continued

| | | |
|---|---|---|
| Phase F | Water | 10.0% |
| | Polyquaternium-10 (Polymer JR 400, Amerchol) | 0.2% |
| Phase G | Citric Acid | to pH 5.0 |
| Phase H | Preservative | q.s. |

Recipes 47a and 47b: Shampoo

| Recipes | 47a | 47b |
|---|---|---|
| Water | to 100.0% | to 100.0% |
| Composition from example 1, 2 or 3 | 2.5% | 2.5% |
| Composition from example 4 | 1.5% | 1.5% |
| Cocamidopropyl Betaine (TEGO ® Betain F 50, Evonik, 38%) | 22.0% | 22.0% |
| Lauryl Glucoside (Plantacare 1200 UP, BASF, 50%) | 6.0% | 6.0% |
| Sodium Cocoyl Glutamate (Plantapon ACG HC, BASF) | 1.5% | 1.5% |
| Sodium Cocoyl Glycinate (Hostapon SG, Clariant) | 0.8% | 0.8% |
| Zinc Pyrithione (Microcare ZP, Thor) | 0.1% | 0.1% |
| PEG-120 Methyl Glucose Dioleate (ANTIL ® 120 Plus, Evonik) | 0.4% | 0.4% |
| Sodium Chloride | 0.5% | 0.5% |
| Isostearamide MIPA; Glyceryl Laurate (ANTIL ® SPA 80, Evonik) | 0.5% | 0.5% |
| Xanthan Gum (Keltrol CG-SFT, CP Kelco) | 0.3% | 0.3% |
| Hydroxypropyl Guar Hydroxypropyltrimonium Chloride (Jaguar C-162, Solvay Rhodia) | 0.3% | 0.3% |
| Quaternium-80 (ABIL ® Quat 3272, Evonik) | 0.4% | 0.4% |
| Palmitamidopropyltrimonium Chloride (VARISOFT ® PATC, Evonik) | 0.4% | 0.4% |
| Argania spinosa oil (Argan Oil, DSM Nutritional Products Ltd.) | 0.1% | 0.1% |
| Glycerin (Glycerol EP, vegetable, Spiga Nord) | 0.6% | 0.6% |
| Tetrasodium EDTA (Versene 100, The Dow Chemical Company) | 0.1% | 0.1% |
| Caffeine (Merck KGaA/EMD Chemicals, Inc.) | 0.1% | 0.1% |
| Hydrolyzed Wheat Protein (Gluadin WLM, BASF) | 0.1% | 0.1% |
| Limonene (Dipentene No. 122, Hercules Inc.) | 0.1% | 0.1% |
| Citric Acid | to pH 5.5 | to pH 5.5 |
| Sodium Phytate; Aqua; Alcohol (dermofeel ® PA-3; Evonik Dr. Straetmans GmbH (PA-3) | | 0.1% |
| Perfume | 0.2% | |
| Preservative | q.s. | |
| Aqua; Sodium Levulinate; Sodium Benzoate (Verstatil ® BL non-GMO; Evonik Dr. Straetmans GmbH) | | 1.2% |

Formulation 48: Liquid Soap

| | |
|---|---|
| Water | to 100% |
| Glycerin (Glycerol EP, vegetable, Spiga Nord) | 4.0% |
| Alcohol | 4.0% |
| Sodium Coco-Sulfate (Texapon HC G, BASF) | 3.0% |
| Lauryl Glucoside (Plantacare 1200 UP, BASF, 50%) | 6.0% |
| Composition from example 1, 2 or 3 | 3.0% |
| Xanthan Gum (Keltrol CG-SFT, CP Kelco) | 1.5% |
| Mangifera Indica (mango) Fruit Extract (Mango Extract, Draco Natural Products) | 0.5% |
| Limonene (Dipentene No. 122, Hercules Inc.) | 0.1% |
| Linalool (Lipofresh, Lipo Chemicals, Inc.) | 0.1% |
| Citric Acid | to pH 4.9 |
| Preservative | q.s. |
| Dyes | q.s. |

Formulation 49: Cream Soap

| | |
|---|---|
| Water | to 100% |
| Propylene Glycol (Euxyl K 320, Schülke & Mayr GmbH) | 2.0% |
| Coco-Glucoside (Plantacare 818 UP, BASF, 51%) | 10.0% |
| Glycerin (Glycerol EP, vegetable, Spiga Nord) | 5.0% |
| Composition from example 1, 2 or 3 | 2.5% |
| Disodium Cocoyl Glutamate (Planatpon ACG LC, BASF) | 2.5% |
| Xanthan Gum (Keltrol CG-SFT, CP Kelco) | 1.2% |
| Stearic Acid (Pristerene 4922, Croda Europe, Ltd.) | 1.2% |
| Citric Acid | to pH 5.5 |
| Olea Europaea Fruit Oil (Cropure Olive, Croda Europe, Ltd.) | 0.2% |
| Glyceryl Oleate (TEGIN ® O V, Evonik) | 1.0% |
| Sodium Cocoyl Glutamate (Plantapon ACG HC, BASF) | 0.8% |
| Tetrasodium EDTA (Versene 100, The Dow Chemical Company) | 0.2% |
| Perfume | 0.1% |
| Preservative | q.s. |
| Dyes | q.s. |

Formulation 50: Oil Bath

| | |
|---|---|
| Water | to 100.0% |
| Glycine Soja Oil (Cropure Soybean, Croda Europe, Ltd.) | 20.0% |
| Composition from example 1, 2 or 3 | 12.0% |
| Polyglyceryl-3 Palmitate (Dermofeel ® PP, Evonik Dr. Straetmans) | 4.5% |
| Glyceryl Caprylate (Dermosoft ® GMCY, Evonik Dr. Straetmans) | 3.0% |
| Simmondsia Chinensis Seed Oil (AEC Jojoba Oil Refined, A & E Connock, Perfumery & Cosmetics Ltd.) | 1.2% |
| Prunus Amygdalus Dulcis (sweet almond) Oil (Cropure Almond, Croda Europe, Ltd.) | 1.0% |
| Triticum Vulgare Germ Oil (Cropure Wheatgerm, Croda Europe, Ltd.) | 0.5% |
| Tocopherol (Euxyl K 700, Schülke & Mayr GmbH) | 0.2% |
| Limonene (Dipentene No. 122, Hercules Inc.) | 0.1% |
| Citral | 0.1% |
| Preservative | q.s. |
| Dyes | q.s. |

Formulation 51: Micellar Water for Makeup Removal

| | |
|---|---|
| Water | to 100.0% |
| Perfume | 0.1% |
| Composition from example 1, 2 or 3 | 2.0% |
| Capryl/Capramidopropyl Betaine (TEGO ® Betain 810, Evonik, 38%) | 1.3% |
| Polyglyceryl-6 Caprylate; Polyglyceryl-3 Cocoate; Polyglyceryl-4 Caprate; Polyglyceryl-6 Ricinoleate (TEGO ® Solve 61, Evonik) | 1.0% |
| Betaine (TEGO ® Natural Betaine, Evonik) | 2.0% |
| Glycerin (Glycerol EP, vegetable, Spiga Nord) | 1.0% |
| Preservative | q.s. |

Recipes 52a and 52b: Solution for Wet Wipes

| Recipe | 52a | 52b |
|---|---|---|
| Composition from example 1, 2 or 3 | 3.5% | 3.5% |
| Aloe Barbadensis Leaf Extract (Aloe-Con UP 40, Florida Food Products Inc.) | 0.2% | 0.2% |
| Isopropyl Myristate (TEGOSOFT ® M, Evonik) | 0.2% | 0.2% |
| Disodium Cocoamphodiacetate (REWOTERIC ® AM 2 C NM, Evonik, 39%) | 1.5% | 1.5% |
| Perfume | 0.2% | 0.2% |
| Propylene Glycol (Euxyl K 320, Schülke & Mayr GmbH) | 2.5% | 2.5% |
| Hydrolyzed Silk (Crosilk 10000, Croda Inc.) | 0.2% | 0.2% |
| Caprylyl/Capryl Glucoside (Plantacare 810 UP, BASF) | 1.0% | 1.0% |
| Water | to 100.0% | to 100.0% |
| Citric Acid | to pH 5.0 | to pH 5.0 |
| Phenoxyethanol (S&M Phenoxyethanol, Schülke & Mayr GmbH) | 0.5% | 0.5% |
| Dehydroacetic Acid (Unisept DHA (Universal Preserv-A-Chem, Inc.) | 0.1% | 0.1% |
| Sodium Benzoate (Euxyl K 712, Schülke & Mayr GmbH) | 0.4% | 0.4% |
| Salicylic Acid (salicylic acid nat.; Evonik Dr. Straetmans GmbH) | | 0.5% |

Formulation 53: Antiperspirant Deodorant

| | | |
|---|---|---|
| Phase A | Composition from example 1, 2 or 3 | 4.0% |
| | Dicaprylyl Ether (Cetiol OE, BASF) | 0.3% |
| | Geraniol (Nerol 800, International Flavors & Fragrances Inc.) | 0.1% |
| | Linalool (Lipofresh, Lipo Chemicals, Inc.) | 0.1% |
| | Perfume | 0.1% |
| Phase B | Propylene Glycol (Euxyl K 320, Schülke & Mayr GmbH) | 1.0% |
| | Butylene Glycol (Oxea Corparation) | 0.2% |
| | Water | 5.0% |
| | Palmitamidopropyltrimonium Chloride (VARISOFT ® PATC, Evonik) | 1.0% |
| Phase C | Water | 50.0% |
| | Hydroxethyl ethylcellulose (Structure Cel 4400 E, AkzoNobel) | 0.8% |
| | Sodium Hydroxide (10% in water) | 0.3% |
| Phase D | Aluminium Chlorohydrate (Locron L, Clariant) | 15.0% |
| Phase E | Preservative | q.s. |
| | Water | to 100.0% |

Formulation 54: Mouthwash

| | |
|---|---|
| Composition from example 1, 2 or 3 | 0.4% |
| Glycolipids (Rheance One, Evonik) | 0.2% |
| Flavour | 0.2% |
| Water | to 100.0% |
| Sorbitol (Karion FP Liquid, Merck) | 3.0% |
| Preservative | q.s. |
| Dyes | q.s. |

Formulation 55: Toothpaste

| | | |
|---|---|---|
| A | Sorbitol (Karion FP Liquid, Merck) | 50.0% |
| | Water | to 100.0% |
| | Sodium carboxymethyl cellulose (Blanose 7MXF, Ashland) | 1.2% |
| B | Sodium Saccharin (Sigma Aldrich) | 0.1% |
| | Sodium Fluoride (Sigma Aldrich) | 0.1% |
| C | Titanium Dioxide (Caesar & Loretz) | 0.4% |
| | Hydrated Silica (Zeodent ® 113, Evonik) | 14.0% |
| | Hydrated Silica (Zeodent ® 165, Evonik) | 8.0% |
| D | Flavour oil | 1.0% |
| E | Glyceryl Caprylate (dermosoft ® GMCY, Evonik) | 0.3% |
| | Composition from example 1, 2 or 3 | 3.5% |

The invention claimed is:

1. A process for the enzymatic preparation of a xylitol carboxylate, comprising:

A) providing xylitol and at least one acyl group donor,

B) reacting the xylitol with the at least one acyl group donor in the presence of a lipase at a temperature of from 75° C. to 110° C., to give a xylitol carboxylate, wherein the reacting is carried out in the absence of solvent, and C) optionally, purifying the xylitol carboxylate, wherein in B), the xylitol and the at least one acyl group donor make up at least 95% by weight, based on an overall reaction mixture at the start of B), wherein the at least one acyl group donor comprises a fatty acid having 6 to 22 carbon atoms, and wherein the lipase is lipase A and/or B from *Candida antarctica.*

2. The process according to claim 1, wherein A) comprises blending the xylitol and the at least one acyl group donor for at least ten minutes.

3. The process according to claim 1, wherein B) is carried out at a pressure of less than 1 bar.

4. The process according to claim 2, wherein in A), the blending is carried out within a temperature range from 80° C. to 120° C.

5. The process according to claim 1, wherein the at least one acyl group donor comprises caprylic acid.

6. The process according to claim 1, wherein the at least one acyl group donor comprises a mixture of caprylic acid and capric acid.

7. The process according to claim 1, wherein the reacting is carried out at a temperature of from 89° C. to 95° C.

8. The process according to claim 1, wherein the at least one acyl group donor consists of caprylic acid or a mixture of caprylic and capric acid.

9. The process according to claim 1, wherein the at least one acyl group donor is other than oleic acid.

10. The process according to claim 1, wherein the produced xylitol carboxylate comprises:

at least one carboxylic ester of xylitol, and at least one of a carboxylic ester of 1,4-anhydroxylitol, a carboxylic ester of 1,4-anhydroarabitol, and a carboxylic ester of 1,4-anhydroribitol, wherein a ratio by weight of xylitol residues present in the xylitol carboxylate to a sum total of all 1,4-anhydroxylitol residues, 1,4-anhydroarabitol residues, and 1,4-anhydroribitol residues present in the xylitol carboxylate is greater than or equal to 96:4, and wherein a molar ratio of esterified primary hydroxyl groups to esterified secondary hydroxyl groups in the at least one carboxylic ester of xylitol is 80:20 to 20:80.

11. The process according to claim 10, wherein a carboxylic acid component is derived from a carboxylic acid containing 2 to 34 carbon atoms or a mixture thereof.

12. The process according to claim 10, wherein an average degree of esterification of the at least one carboxylic ester of xylitol present is from 1.0 to 4.0.

13. The process according to claim 10, wherein the at least one carboxylic ester of xylitol present comprises monoesters of xylitol, diesters of xylitol and triesters of xylitol.

14. The process according to claim 10, wherein the xylitol carboxylate comprises 0.05% to 40% by weight of free xylitol.

15. The process according to claim 10, wherein the xylitol carboxylate comprises less than 25% by weight of at least one free carboxylic acid.

16. The process according to claim 10, wherein a total monoester component of the at least one carboxylic ester of xylitol contains from 5% by weight to 25% by weight of secondary ester regioisomers.

17. The process according to claim 10, wherein a total monoester component of the at least one carboxylic ester of xylitol and a total diester component of the at least one carboxylic ester of xylitol each comprise at least two regioisomers.

18. The process according to claim 10, wherein the molar ratio of esterified primary hydroxyl groups to esterified secondary hydroxyl groups in the at least one carboxylic ester of xylitol is from 65:35 to 40:60.

19. The process according to claim 11, wherein the carboxylic acid component is derived from a natural fatty acid or a mixture thereof.

20. The process according to claim 13, wherein the triesters of xylitol are present in an amount of from 10% to 50% by weight, based on all carboxylic esters of xylitol present.

* * * * *